US011177035B2

(12) United States Patent
Reicher et al.

(10) Patent No.: US 11,177,035 B2
(45) Date of Patent: Nov. 16, 2021

(54) SYSTEMS AND METHODS FOR MATCHING, NAMING, AND DISPLAYING MEDICAL IMAGES

(71) Applicant: INTERNATIONAL BUSINESS MACHINES CORPORATION, Armonk, NY (US)

(72) Inventors: Murray A. Reicher, Rancho Santa Fe, CA (US); Evan K. Fram, Paradise Valley, AZ (US); Steven M. Greim, Oceanside, CA (US); John J. Schumacher, San Diego, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 68 days.

(21) Appl. No.: 16/692,283

(22) Filed: Nov. 22, 2019

(65) Prior Publication Data

US 2020/0090332 A1    Mar. 19, 2020

Related U.S. Application Data

(63) Continuation of application No. 15/346,530, filed on Nov. 8, 2016, now Pat. No. 10,540,763, which is a (Continued)

(51) Int. Cl.
*G16H 30/40* (2018.01)
*G06T 7/38* (2017.01)
(Continued)

(52) U.S. Cl.
CPC .......... *G16H 30/40* (2018.01); *G06F 3/0484* (2013.01); *G06T 1/0007* (2013.01); *G06T 7/0012* (2013.01); *G06T 7/30* (2017.01); *G06T 7/38* (2017.01); *G06T 15/00* (2013.01); *G06T 19/003* (2013.01); *G06T 19/20* (2013.01);
(Continued)

(58) Field of Classification Search
CPC ........ A63F 13/00; A63F 13/327; A63F 13/65; G06T 7/246; G06T 7/269; G06T 11/00; G06K 9/3241
See application file for complete search history.

(56) References Cited

U.S. PATENT DOCUMENTS 4,672,683 A   6/1987 Matsueda
5,123,056 A   6/1992 Wilson
(Continued)

FOREIGN PATENT DOCUMENTS

WO   WO 2007/131157 A2   11/2007

OTHER PUBLICATIONS

US 7,801,341 B2, 09/2010, Fram et al. (withdrawn)
(Continued)

*Primary Examiner* — Manav Seth
(74) *Attorney, Agent, or Firm* — Michael Best & Friedrich LLP

(57) ABSTRACT

A method of matching medical images according to user-defined matches rules. In one embodiment, the matched medical images are displayed according user-defined display rules such that the matched medical images may be visually compared in manner that is suitable to the viewer's viewing preferences.

20 Claims, 2 Drawing Sheets

Related U.S. Application Data continuation of application No. 14/244,431, filed on Apr. 3, 2014, now Pat. No. 9,542,082, which is a continuation of application No. 13/345,606, filed on Jan. 6, 2012, now Pat. No. 8,731,259, which is a continuation of application No. 12/870,645, filed on Aug. 27, 2010, now Pat. No. 8,094,901, which is a continuation of application No. 11/265,978, filed on Nov. 3, 2005, now Pat. No. 7,787,672.

(60) Provisional application No. 60/625,690, filed on Nov. 4, 2004.

(51) Int. Cl.

| | | |
|---|---|---|
| *G06T 7/30* | (2017.01) | |
| *G16H 40/63* | (2018.01) | |
| *G16H 30/20* | (2018.01) | |
| *G16H 50/70* | (2018.01) | |
| *G06F 3/0484* | (2013.01) | |
| *G06T 7/00* | (2017.01) | |
| *G06T 15/00* | (2011.01) | |
| *G06T 19/00* | (2011.01) | |
| *G06T 19/20* | (2011.01) | |
| *G06T 1/00* | (2006.01) | |

(52) U.S. Cl.
CPC .......... *G16H 30/20* (2018.01); *G16H 40/63* (2018.01); *G16H 50/70* (2018.01); *G06T 2207/10081* (2013.01); *G06T 2207/10116* (2013.01); *G06T 2207/30012* (2013.01); *G06T 2219/2004* (2013.01)

(56) References Cited

U.S. PATENT DOCUMENTS

| | | |
|---|---|---|
| 5,172,419 A | 12/1992 | Manian |
| 5,179,651 A | 1/1993 | Taaffe et al. |
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,671,353 A * | 9/1997 | Tian .................... G16H 30/20 714/48 |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,867,322 A | 2/1999 | Morton |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Agiro |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,210,327 B1 * | 4/2001 | Brackett .................. A61B 8/56 600/437 |
| 6,211,795 B1 | 4/2001 | Izuta |
| 6,211,884 B1 | 4/2001 | Knittel et al. |
| 6,219,059 B1 | 4/2001 | Argiro |
| 6,219,061 B1 | 4/2001 | Laurer et al. |
| 6,243,095 B1 | 6/2001 | Shile et al. |
| 6,243,098 B1 | 6/2001 | Laurer et al. |
| 6,249,594 B1 * | 6/2001 | Hibbard ................. G06T 7/0012 382/128 |
| 6,262,740 B1 | 7/2001 | Laurer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Laurer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Laurer et al. |
| 6,424,346 B1 | 7/2002 | Correll et al. |
| 6,424,996 B1 | 7/2002 | Killlcommons et al. |
| 6,426,749 B1 | 7/2002 | Knittel et al. |
| 6,427,022 B1 | 7/2002 | Craine et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke, Jr. et al. |
| 6,577,753 B2 | 6/2003 | Ogawa |
| 6,603,494 B1 | 8/2003 | Banks et al. |
| 6,604,115 B1 * | 8/2003 | Gary, Jr. .................. G06F 16/00 |
| 6,606,171 B1 * | 8/2003 | Renk .................. H04N 1/00002 358/475 |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,657,655 B1 * | 12/2003 | Iizuka .................. H04N 19/597 348/47 |
| 6,678,764 B2 | 1/2004 | Parvelescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Oian et al. |
| 6,714,623 B2 * | 3/2004 | Sako .................... A61B 6/00 378/115 |
| 6,734,880 B2 * | 5/2004 | Chang .................. G16H 30/20 715/738 |
| 6,760,755 B1 | 7/2004 | Brackett |
| 6,775,402 B2 | 8/2004 | Bacus et al. |
| 6,778,689 B1 | 8/2004 | Aksit et al. |
| 6,785,410 B2 * | 8/2004 | Vining .................. G06F 16/5838 382/128 |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B2 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,911,975 B2 * | 6/2005 | Iizuka .................. G09G 3/003 345/419 |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |

(56) References Cited

U.S. PATENT DOCUMENTS

| | | | |
|---|---|---|---|
| 7,027,633 B2 | 4/2006 | Foran et al. | |
| 7,031,504 B1 | 4/2006 | Argiro et al. | |
| 7,031,846 B2 | 4/2006 | Kaushikkar et al. | |
| 7,039,723 B2 | 5/2006 | Hu et al. | |
| 7,043,474 B2 | 5/2006 | Mojsilovic et al. | |
| 7,047,235 B2 * | 5/2006 | Yang | G16H 30/20 707/661 |
| 7,050,620 B2 | 5/2006 | Heckman | |
| 7,054,473 B1 | 5/2006 | Roehrig et al. | |
| 7,058,901 B1 | 6/2006 | Hafey et al. | |
| 7,092,572 B2 | 8/2006 | Huang et al. | |
| 7,103,205 B2 | 9/2006 | Wang et al. | |
| 7,106,479 B2 | 9/2006 | Roy et al. | |
| 7,110,616 B2 | 9/2006 | Ditt et al. | |
| 7,113,186 B2 | 9/2006 | Kim et al. | |
| 7,123,684 B2 | 10/2006 | Jing et al. | |
| 7,136,064 B2 | 11/2006 | Zuiderveld | |
| 7,139,416 B2 | 11/2006 | Vuylsteke | |
| 7,149,334 B2 | 12/2006 | Dehmeshki | |
| 7,155,043 B2 | 12/2006 | Daw | |
| 7,162,623 B2 | 1/2007 | Yngvesson | |
| 7,170,532 B2 | 1/2007 | Sako | |
| 7,174,054 B2 | 2/2007 | Manber et al. | |
| 7,209,149 B2 | 4/2007 | Jogo | |
| 7,209,578 B2 | 4/2007 | Saito et al. | |
| 7,212,661 B2 | 5/2007 | Samara et al. | |
| 7,218,763 B2 | 5/2007 | Belykh et al. | |
| 7,224,852 B2 | 5/2007 | Lipton et al. | |
| 7,236,558 B2 | 6/2007 | Saito et al. | |
| 7,260,249 B2 * | 8/2007 | Smith | G16H 30/40 382/128 |
| 7,263,710 B1 | 8/2007 | Hummel, Jr. et al. | |
| 7,272,610 B2 | 9/2007 | Torres | |
| 7,277,564 B2 * | 10/2007 | Yarger | G06T 7/00 378/20 |
| 7,346,199 B2 | 3/2008 | Pfaff | |
| 7,362,324 B2 * | 4/2008 | Iizuka | G09G 3/003 345/419 |
| 7,366,992 B2 | 4/2008 | Thomas, III | |
| 7,379,578 B2 | 5/2008 | Soussaline et al. | |
| 7,412,111 B2 | 8/2008 | Battle et al. | |
| 7,450,747 B2 | 11/2008 | Jabri et al. | |
| 7,492,970 B2 | 2/2009 | Saito et al. | |
| 7,505,782 B2 | 3/2009 | Chu | |
| 7,516,417 B2 | 4/2009 | Amador et al. | |
| 7,519,591 B2 * | 4/2009 | Landi | H04L 9/14 |
| 7,523,505 B2 | 4/2009 | Menschik et al. | |
| 7,525,554 B2 | 4/2009 | Morita et al. | |
| 7,526,114 B2 | 4/2009 | Xia et al. | |
| 7,526,132 B2 | 4/2009 | Koenig | |
| 7,545,965 B2 | 6/2009 | Suzuki et al. | |
| 7,574,029 B2 | 8/2009 | Peterson et al. | |
| 7,583,861 B2 | 9/2009 | Hanna et al. | |
| 7,590,272 B2 | 9/2009 | Brejl et al. | |
| 7,599,534 B2 | 10/2009 | Krishnan | |
| 7,613,335 B2 | 11/2009 | McLennan et al. | |
| 7,634,121 B2 | 12/2009 | Novatzky et al. | |
| 7,636,413 B2 | 12/2009 | Toth | |
| 7,639,879 B2 | 12/2009 | Goto et al. | |
| 7,656,543 B2 | 2/2010 | Atkins | |
| 7,660,413 B2 | 2/2010 | Partovi et al. | |
| 7,660,448 B2 | 2/2010 | Collins et al. | |
| 7,660,481 B2 | 2/2010 | Schaap et al. | |
| 7,660,488 B2 | 2/2010 | Reicher et al. | |
| 7,668,352 B2 | 2/2010 | Tecotzky et al. | |
| 7,683,909 B2 | 3/2010 | Takekoshi | |
| 7,698,152 B2 | 4/2010 | Reid | |
| 7,716,277 B2 | 5/2010 | Yamatake | |
| 7,787,672 B2 | 8/2010 | Reicher et al. | |
| 7,834,891 B2 | 11/2010 | Yarger et al. | |
| 7,835,560 B2 | 11/2010 | Vining et al. | |
| 7,885,440 B2 | 2/2011 | Fram et al. | |
| 7,885,828 B2 | 2/2011 | Glaser-Seidnitzer et al. | |
| 7,899,514 B1 | 3/2011 | Kirkland | |
| 7,920,152 B2 | 4/2011 | Fram et al. | |
| 7,941,462 B2 | 5/2011 | Akinyemi et al. | |
| 7,983,614 B2 | 5/2011 | Reicher | |
| 7,965,408 B2 * | 6/2011 | Samari | G16H 10/20 358/1.18 |
| 7,965,907 B2 * | 6/2011 | Takekoshi | G06Q 10/10 382/305 |
| 7,970,188 B2 | 6/2011 | Mahesh et al. | |
| 7,970,625 B2 | 6/2011 | Reicher et al. | |
| 7,991,210 B2 | 8/2011 | Peterson et al. | |
| 7,992,100 B2 | 8/2011 | Lundstrom et al. | |
| 7,995,821 B2 | 8/2011 | Nakamura | |
| 8,019,138 B2 | 9/2011 | Reicher et al. | |
| 8,045,214 B2 * | 10/2011 | Samari | G16H 10/20 358/1.18 |
| 8,046,044 B2 | 10/2011 | Stazzone et al. | |
| 8,050,938 B1 | 11/2011 | Green, Jr. et al. | |
| 8,065,166 B2 | 11/2011 | Maresh et al. | |
| 8,073,225 B2 | 12/2011 | Hagen et al. | |
| 8,094,901 B1 | 1/2012 | Reicher et al. | |
| 8,150,708 B2 | 4/2012 | Kotula et al. | |
| 8,214,756 B2 | 7/2012 | Salazar-Ferrer et al. | |
| 8,217,966 B2 | 7/2012 | Fram et al. | |
| 8,244,014 B2 | 8/2012 | Reicher et al. | |
| 8,249,687 B2 | 8/2012 | Peterson et al. | |
| 8,262,572 B2 | 9/2012 | Chono | |
| 8,292,811 B2 | 10/2012 | Relkuntwar et al. | |
| 8,297,147 B2 | 10/2012 | Wu | |
| 8,298,147 B2 | 10/2012 | Huennekens et al. | |
| 8,370,293 B2 | 2/2013 | Iwase et al. | |
| 8,379,051 B2 | 2/2013 | Brown | |
| 8,380,533 B2 | 2/2013 | Reicher et al. | |
| 8,391,643 B2 | 3/2013 | Melbourne et al. | |
| 8,406,491 B2 | 3/2013 | Gee et al. | |
| 8,452,063 B2 | 5/2013 | Wojton et al. | |
| 8,457,990 B1 | 6/2013 | Reicher et al. | |
| 8,520,978 B2 | 8/2013 | Jakobovits | |
| 8,554,576 B1 | 10/2013 | Reicher et al. | |
| 8,560,050 B2 | 10/2013 | Martin et al. | |
| 8,610,746 B2 | 12/2013 | Fram et al. | |
| 8,626,527 B1 | 1/2014 | Reicher et al. | |
| 8,693,757 B2 | 4/2014 | Gundel | |
| 8,712,120 B1 | 4/2014 | Reicher et al. | |
| 8,731,259 B2 | 5/2014 | Reicher et al. | |
| 8,751,268 B1 | 6/2014 | Reicher et al. | |
| 8,771,189 B2 | 7/2014 | Ionasec et al. | |
| 8,797,350 B2 | 8/2014 | Fram | |
| 8,879,807 B2 | 11/2014 | Fram et al. | |
| 8,913,808 B2 | 12/2014 | Reicher et al. | |
| 8,954,884 B2 | 2/2015 | Barger | |
| 8,976,190 B1 | 3/2015 | Westerhoff et al. | |
| 9,042,617 B1 | 5/2015 | Reicher et al. | |
| 9,075,899 B1 | 7/2015 | Reicher | |
| 9,092,551 B1 | 7/2015 | Reicher | |
| 9,092,727 B1 | 7/2015 | Reicher | |
| 9,324,188 B1 | 4/2016 | Fram et al. | |
| 9,386,084 B1 | 7/2016 | Reicher et al. | |
| 9,471,210 B1 | 10/2016 | Fram et al. | |
| 9,495,604 B1 | 11/2016 | Fram | |
| 9,501,617 B1 | 11/2016 | Reicher et al. | |
| 9,501,627 B2 | 11/2016 | Reicher et al. | |
| 9,501,863 B1 | 11/2016 | Fram et al. | |
| 9,536,324 B1 | 1/2017 | Fram | |
| 9,542,082 B1 | 1/2017 | Reicher et al. | |
| 9,672,477 B1 | 6/2017 | Reicher et al. | |
| 9,684,762 B2 | 6/2017 | Reicher et al. | |
| 9,727,938 B1 | 8/2017 | Reicher et al. | |
| 9,734,576 B2 | 8/2017 | Fram et al. | |
| 9,754,074 B1 | 9/2017 | Reicher et al. | |
| 9,836,202 B1 | 12/2017 | Reicher et al. | |
| 9,892,341 B2 | 2/2018 | Reicher et al. | |
| 9,934,568 B2 | 4/2018 | Reicher et al. | |
| 10,096,111 B2 | 10/2018 | Fram et al. | |
| 10,157,686 B1 | 12/2018 | Reicher et al. | |
| 10,387,612 B2 | 8/2019 | Wu et al. | |
| 10,437,444 B2 | 10/2019 | Reicher et al. | |
| 10,438,352 B2 | 10/2019 | Fram et al. | |
| 10,540,763 B2 | 1/2020 | Reicher et al. | |
| 10,579,903 B1 | 3/2020 | Reicher | |
| 10,592,688 B2 | 3/2020 | Reicher et al. | |

(56) References Cited

U.S. PATENT DOCUMENTS

| | | |
|---|---|---|
| 10,607,341 B2 | 3/2020 | Reicher et al. |
| 10,614,615 B2 | 4/2020 | Fram et al. |
| 10,665,342 B2 | 5/2020 | Fram |
| 10,672,512 B2 | 6/2020 | Fram |
| 2001/0016822 A1 | 8/2001 | Bessette |
| 2001/0041991 A1 | 11/2001 | Segal et al. |
| 2001/0042124 A1 | 11/2001 | Barron |
| 2002/0016718 A1* | 2/2002 | Rothschild ......... H04N 1/32128 705/2 |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0054038 A1 | 5/2002 | Nemoto |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0099273 A1 | 7/2002 | Bocionek et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0106373 A1 | 8/2002 | Hillman et al. |
| 2002/0110285 A1 | 8/2002 | Wang et al. |
| 2002/0144697 A1 | 10/2002 | Betz |
| 2002/0145941 A1 | 10/2002 | Poland et al. |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0188637 A1 | 12/2002 | Bailey et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0053668 A1 | 3/2003 | Ditt et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140044 A1 | 7/2003 | Mok et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215120 A1 | 11/2003 | Uppaluri et al. |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |
| 2004/0027359 A1 | 2/2004 | Aharon et al. |
| 2004/0061889 A1 | 4/2004 | Wood et al. |
| 2004/0068170 A1 | 4/2004 | Wang et al. |
| 2004/0077952 A1 | 4/2004 | Rafter et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0122787 A1 | 6/2004 | Avinash et al. |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzkky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamoorthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0203775 A1 | 9/2005 | Chesbrough |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0259118 A1 | 11/2005 | Mojaver et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093027 A1 | 5/2006 | Draving et al. |
| 2006/0093139 A1 | 5/2006 | Quan |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111937 A1 | 5/2006 | Yarger et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey et al. |
| 2006/0188134 A1 | 8/2006 | Quist |
| 2006/0230072 A1 | 10/2006 | Partovi et al. |
| 2006/0238546 A1 | 10/2006 | Handley et al. |
| 2006/0239573 A1 | 10/2006 | Novatzky et al. |
| 2006/0241979 A1 | 10/2006 | Sato et al. |
| 2006/0267976 A1 | 11/2006 | Saito et al. |
| 2006/0274145 A1 | 12/2006 | Reiner |
| 2006/0276708 A1 | 12/2006 | Peterson et al. |
| 2006/0277075 A1 | 12/2006 | Salwan |
| 2006/0282408 A1 | 12/2006 | Wisely et al. |
| 2006/0282447 A1 | 12/2006 | Hollebeek |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |

(56) References Cited

U.S. PATENT DOCUMENTS

| | | |
|---|---|---|
| 2007/0109299 A1 | 5/2007 | Peterson et al. |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper et al. |
| 2007/0237380 A1 | 10/2007 | Iwase et al. |
| 2007/0239481 A1 | 10/2007 | DiSilvestro et al. |
| 2007/0245308 A1 | 10/2007 | Hill et al. |
| 2007/0270695 A1 | 11/2007 | Keen |
| 2008/0016111 A1 | 1/2008 | Keen |
| 2008/0019581 A1 | 1/2008 | Gkanatsios et al. |
| 2008/0021877 A1 | 1/2008 | Saito et al. |
| 2008/0031507 A1 | 2/2008 | Uppaluri et al. |
| 2008/0059245 A1 | 3/2008 | Sakaida et al. |
| 2008/0097186 A1 | 4/2008 | Biglieri et al. |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1 | 5/2008 | Sadikali et al. |
| 2008/0130966 A1 | 6/2008 | Crucs |
| 2008/0133526 A1 | 6/2008 | Haitani et al. |
| 2008/0136838 A1 | 6/2008 | Goede et al. |
| 2008/0136868 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0022386 A1 | 1/2009 | Karau et al. |
| 2009/0028410 A1 | 1/2009 | Shimazaki |
| 2009/0080719 A1 | 3/2009 | Watt |
| 2009/0091566 A1 | 4/2009 | Turney et al. |
| 2009/0094513 A1 | 4/2009 | Bay |
| 2009/0123052 A1 | 5/2009 | Ruth et al. |
| 2009/0129643 A1 | 5/2009 | Natanzon et al. |
| 2009/0129651 A1 | 5/2009 | Zagzebski et al. |
| 2009/0132586 A1 | 5/2009 | Napora et al. |
| 2009/0150481 A1 | 6/2009 | Garcia et al. |
| 2009/0164247 A1 | 6/2009 | Dobler et al. |
| 2009/0177637 A1* | 7/2009 | Hollebeek ............. G16H 30/40 |
| 2009/0182577 A1 | 7/2009 | Squilla et al. |
| 2009/0198514 A1 | 8/2009 | Rhodes |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0297013 A1 | 12/2009 | Chaudhuri |
| 2009/0326373 A1 | 12/2009 | Boese et al. |
| 2010/0053353 A1 | 3/2010 | Hunter et al. |
| 2010/0086182 A1 | 4/2010 | Luo et al. |
| 2010/0119027 A1 | 5/2010 | Peterson et al. |
| 2010/0131887 A1 | 5/2010 | Salazar-Ferrer et al. |
| 2010/0138239 A1 | 6/2010 | Reicher et al. |
| 2010/0138240 A1 | 6/2010 | Leib et al. |
| 2010/0198608 A1 | 8/2010 | Kaboff et al. |
| 2010/0201714 A1 | 8/2010 | Reicher et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram et al. |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0293162 A1 | 12/2011 | Pajeau |
| 2011/0316873 A1 | 12/2011 | Reicher et al. |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |
| 2012/0163684 A1 | 6/2012 | Natanzon et al. |
| 2012/0183191 A1 | 7/2012 | Nakamura |
| 2012/0194540 A1 | 8/2012 | Reicher et al. |
| 2012/0196258 A1 | 8/2012 | Geijsen et al. |
| 2012/0208592 A1 | 8/2012 | Davis et al. |
| 2012/0284657 A1 | 11/2012 | Hafey et al. |
| 2012/0320093 A1 | 12/2012 | Zhu et al. |
| 2012/0324400 A1 | 12/2012 | Caliendo, Jr. et al. |
| 2013/0070998 A1 | 3/2013 | Shibata |
| 2013/0076681 A1 | 3/2013 | Sirpal et al. |
| 2013/0083023 A1 | 4/2013 | Fram et al. |
| 2013/0129198 A1 | 5/2013 | Sherman et al. |
| 2013/0129231 A1 | 5/2013 | Dale et al. |
| 2013/0159019 A1 | 6/2013 | Reicher et al. |
| 2013/0169661 A1 | 7/2013 | Reicher et al. |
| 2013/0195329 A1 | 8/2013 | Canda et al. |
| 2013/0198682 A1 | 8/2013 | Matas et al. |
| 2013/0297331 A1 | 11/2013 | Zuehlsdorff et al. |
| 2014/0022194 A1 | 1/2014 | Ito |
| 2014/0096049 A1 | 4/2014 | Vonshak et al. |
| 2014/0119514 A1 | 5/2014 | Miyazawa |
| 2014/0142983 A1 | 5/2014 | Backhaus et al. |
| 2014/0378810 A1 | 12/2014 | Davis et al. |
| 2015/0046349 A1 | 2/2015 | Michael, Jr. et al. |
| 2015/0101066 A1 | 4/2015 | Fram |
| 2015/0160848 A1 | 6/2015 | Gkanatsios et al. |
| 2015/0363104 A1 | 12/2015 | Ichioka et al. |
| 2016/0034110 A1 | 2/2016 | Edwards |
| 2016/0162745 A1 | 9/2016 | Cohen-Solal et al. |
| 2016/0270746 A1 | 9/2016 | Foos et al. |
| 2016/0335395 A1 | 11/2016 | Wu et al. |
| 2017/0038951 A1 | 2/2017 | Reicher et al. |
| 2017/0039321 A1 | 2/2017 | Reicher et al. |
| 2017/0039322 A1 | 2/2017 | Reicher et al. |
| 2017/0039350 A1 | 2/2017 | Reicher et al. |
| 2017/0039705 A1 | 2/2017 | Fram et al. |
| 2017/0046014 A1 | 2/2017 | Fram |
| 2017/0046483 A1 | 2/2017 | Reicher et al. |
| 2017/0046485 A1 | 2/2017 | Reicher et al. |
| 2017/0046495 A1 | 2/2017 | Fram |
| 2017/0046870 A1 | 2/2017 | Fram et al. |
| 2017/0053404 A1 | 2/2017 | Reicher et al. |
| 2017/0200064 A1 | 7/2017 | Reicher et al. |
| 2017/0200269 A1 | 7/2017 | Reicher et al. |
| 2017/0200270 A1 | 7/2017 | Reicher et al. |
| 2017/0206324 A1 | 7/2017 | Reicher et al. |
| 2017/0239720 A1 | 8/2017 | Levin et al. |
| 2017/0293720 A1 | 10/2017 | Reicher et al. |
| 2017/0301090 A1 | 10/2017 | Fram et al. |
| 2017/0308647 A1 | 10/2017 | Reicher et al. |
| 2018/0059918 A1 | 3/2018 | Reicher et al. |
| 2018/0225824 A1 | 8/2018 | Fram et al. |
| 2019/0009371 A1 | 1/2019 | Veerasamy et al. |

OTHER PUBLICATIONS

US 8,208,705 B2, 06/2012, Reicher et al. (withdrawn)

Henri et al., "Design and Implementation of World Wide Web-Based Tools For Image Management in Computed Tomography, Magnetic Resonance Imaging, and Ultrasonography" (pp. 77-79) (Year: 1997).*

Brown et al, "Standardisation in medical image management" (pp. 227-238) (Year: 1998).*

Osteaux et al., "Picture archiving and communication system (PACS): a progressive approach with small systems" (pp. 166-174) (Year: 1996).*

Non-Final Office Action from the U.S. Patent and Trademark Office for U.S. Appl. No. 16/817,963 dated Dec. 10, 2020 (10 pages).

Applicant-Initiated Interview Summary from the U.S. Patent and Trademark Office for U.S. Appl. No. 12/857,915 dated Feb. 4, 2014 (3 pages).

Corrected Notice of Allowability from the U.S. Patent and Trademark Office for U.S. Appl. No. 14/502,055 dated Sep. 19, 2016 (3 pages).

(56) References Cited

OTHER PUBLICATIONS

Corrected Notice of Allowabilliaty from the U.S. Patent and Trademark Office for U.S. Appl. No. 14/502,055 dated Jul. 14, 2016 (2 pages).
Corrected Notice of Allowabilliaty from the U.S. Patent and Trademark Office for U.S. Appl. No. 14/502,055 dated Jun. 27, 2016 (2 pages).
Notice of Allowance from the U.S. Patent and Trademark Office for U.S. Appl. No. 14/502,055 dated Jun. 2, 2016 (10 pages).
Non-Final Office Action from the U.S. Patent and Trademark Office for U.S. Appl. No. 14/502,055 dated Jan. 20, 2016 (9 pages).
Applicant-Initiated Interview Summery from the U.S. Patent and Trademark Office for U.S. Appl. No. 14/502,055 dated Apr. 14, 2016 (3 pages).
Corrected Notice of Allowabilliaty from the U.S. Patent and Trademark Office for U.S. Appl. No. 15/254,627 dated Jul. 13, 2017 (4 pages).
Notice of Allowance from the U.S. Patent and Trademark Office for U.S. Appl. No. 15/254,627 dated Apr. 3, 2017 (11 pages).
Non-Final Office Action from the U.S. Patent and Trademark Office for U.S. Appl. No. 15/254,627 dated Dec. 12, 2016 (12 pages).
Supplemental Notice of Allowabilliaty from the U.S. Patent and Trademark Office for U.S. Appl. No. 11/265,979 dated May 26, 2011 (4 pages).
Notice of Allowance from the U.S. Patent and Trademark Office for U.S. Appl. No. 11/265,979 dated May 13, 2011 (14 pages).
Non-Final Office Action from the U.S. Patent and Trademark Office for U.S. Appl. No. 11/265,979 dated Jul. 8, 2010 (18 pages).
Non-Final Office Action from the U.S. Patent and Trademark Office for U.S. Appl. No. 11/265,979 dated May 13, 2009 (16 pages).
Final Office Action from the U.S. Patent and Trademark Office for U.S. Appl. No. 11/265,979 dated Dec. 23, 2010 (24 pages).
Final Office Action from the U.S. Patent and Trademark Office for U.S. Appl. No. 11/265,979 dated Dec. 22, 2009 (17 pages).
Interview Summary from the U.S. Patent and Trademark Office for U.S. Appl. No. 11/265,979 dated Mar. 17, 2011 (3 pages).
Interview Summary from the U.S. Patent and Trademark Office for U.S. Appl. No. 11/265,979 dated Nov. 16, 2010 (3 pages).
Interview Summary from the U.S. Patent and Trademark Office for U.S. Appl. No. 11/265,979 dated Mar. 4, 2010 (3 pages).
Notice of Allowance from the U.S. Patent and Trademark Office for U.S. Appl. No. 13/171,081 dated Sep. 4, 2013 (11 pages).
Examiner-Initiated Interview Summary from the U.S. Patent and Trademark Office for U.S. Appl. No. 13/171,081 dated Sep. 4, 2013 (1 page).
Non-Final Office Action from the U.S. Patent and Trademark Office for U.S. Appl. No. 13/171,081 dated Jun. 8, 2012 (21 pages).
Final Office Action from the U.S. Patent and Trademark Office for U.S. Appl. No. 13/171,081 dated Oct. 12, 2012 (21 pages).
Applicant-Initiated Interview Summary from the U.S. Patent and Trademark Office for U.S. Appl. No. 13/171,081 dated Nov. 6, 2012 (3 page).
Applicant-Initiated Interview Summary from the U.S. Patent and Trademark Office for U.S. Appl. No. 13/171,081 dated Jul. 31, 2012 (3 page).
Notice of Allowance from the U.S. Patent and Trademark Office for U.S. Appl. No. 14/095,123 dated Mar. 30, 2017 (10 pages).
Non-Final Office Action from the U.S. Patent and Trademark Office for U.S. Appl. No. 14/095,123 dated Feb. 23, 2016 (14 pages).
Non-Final Office Action from the U.S. Patent and Trademark Office for U.S. Appl. No. 14/095,123 dated Mar. 3, 2015 (15 pages).
Final Office Action from the U.S. Patent and Trademark Office for U.S. Appl. No. 14/095,123 dated Jul. 20, 2016 (15 pages).
Final Office Action from the U.S. Patent and Trademark Office for U.S. Appl. No. 14/095,123 dated Jul. 23, 2015 (13 pages).
Applicant-Initiated Interview Summary from the U.S. Patent and Trademark Office for U.S. Appl. No. 14/095,123 dated Aug. 27, 2015 (3 page).
Applicant-Initiated Interview Summary from the U.S. Patent and Trademark Office for U.S. Appl. No. 14/095,123 dated May 1, 2015 (3 page).
Notice of Allowance from the U.S. Patent and Trademark Office for U.S. Appl. No. 11/268,262 dated Feb. 25, 2011 (5 pages).
Notice of Allowance from the U.S. Patent and Trademark Office for U.S. Appl. No. 11/268,262 dated Dec. 1, 2010 (8 pages).
Non-Final Office Action from the U.S. Patent and Trademark Office for U.S. Appl. No. 11/268,262 dated Apr. 16, 2010 (22 pages).
Non-Final Office Action from the U.S. Patent and Trademark Office for U.S. Appl. No. 11/268,262 dated Aug. 24, 2009 (17 pages).
Final Office Action from the U.S. Patent and Trademark Office for U.S. Appl. No. 11/268,262 dated Oct. 28, 2010 (12 pages).
Interview Summary from the U.S. Patent and Trademark Office for U.S. Appl. No. 11/268,262 dated Dec. 1, 2010 (4 pages).
Interview Summary from the U.S. Patent and Trademark Office for U.S. Appl. No. 11/268,262 dated May 12, 2010 (4 pages).
Interview Summary from the U.S. Patent and Trademark Office for U.S. Appl. No. 11/268,262 dated Nov. 24, 2009 (4 pages).
Notice of Allowance from the U.S. Patent and Trademark Office for U.S. Appl. No. 13/079,597 dated Apr. 25, 2012 (5 pages).
Non-Final Office Action from the U.S. Patent and Trademark Office for U.S. Appl. No. 13/079,597 dated Nov. 11, 2012 (8 pages).
Notice of Allowance from the U.S. Patent and Trademark Office for U.S. Appl. No. 13/535,758 dated Aug. 23, 2013 (10 pages).
Non-Final Office Action from the U.S. Patent and Trademark Office for U.S. Appl. No. 13/535,758 dated Apr. 4, 2013 (8 pages).
Corrected Notice of Allowability from the U.S. Patent and Trademark Office for U.S. Appl. No. 14/081,225 dated Oct. 21, 2016 (2 pages).
Notice of Allowance from the U.S. Patent and Trademark Office for U.S. Appl. No. 14/081,225 dated Sep. 2, 2016 (11 pages).
Non-Final Office Action from the U.S. Patent and Trademark Office for U.S. Appl. No. 14/081,225 dated Mar. 10, 2016 (23 pages).
Notice of Allowance from the U.S. Patent and Trademark Office for U.S. Appl. No. 11/265,978 dated Apr. 19, 2010 (7 pages).
Notice of Allowance from the U.S. Patent and Trademark Office for U.S. Appl. No. 11/265,978 dated Nov. 19, 2009 (6 pages).
Non-Final Office Action from the U.S. Patent and Trademark Office for U.S. Appl. No. 11/265,978 dated Jul. 27, 2009 (7 pages).
Notice of Allowance from the U.S. Patent and Trademark Office for U.S. Appl. No. 12/870,645 dated Sep. 13, 2011 (8 pages).
Non-Final Office Action from the U.S. Patent and Trademark Office for U.S. Appl. No. 12/870,645 dated May 5, 2011 (5 pages).
Notice of Allowance from the U.S. Patent and Trademark Office for U.S. Appl. No. 13/345,606 dated Jan. 9, 2014 (7 pages).
Non-Final Office Action from the U.S. Patent and Trademark Office for U.S. Appl. No. 13/345,606 dated May 31, 2013 (12 pages).
Summary of Interview from the U.S. Patent and Trademark Office for U.S. Appl. No. 13/345,606 dated Oct. 21, 2013 (1 page).
Corrected Notice of Allowability from the U.S. Patent and Trademark Office for U.S. Appl. No. 14/244,431 dated Nov. 16, 2016 (4 pages).
Notice of Allowance from the U.S. Patent and Trademark Office for U.S. Appl. No. 14/244,431 dated Aug. 18, 2016 (8 pages).
Non-Final Office Action from the U.S. Patent and Trademark Office for U.S. Appl. No. 14/244,431 dated Mar. 18, 2016 (15 pages).
Applicant-Initiated Interview Summary from the U.S. Patent and Trademark Office for U.S. Appl. No. 14/244,431 dated Jun. 17, 2016 (3 page).
Notice of Allowance from the U.S. Patent and Trademark Office for U.S. Appl. No. 15/799,657 dated Aug. 15, 2018 (8 pages).
Non-Final Office Action from the U.S. Patent and Trademark Office for U.S. Appl. No. 15/799,657 dated Mar. 8, 2018 (25 pages).
Notice of Allowance from the U.S. Patent and Trademark Office for U.S. Appl. No. 15/799,657 dated Feb. 6, 2019 (8 pages).
Final Office Action from the U.S. Patent and Trademark Office for U.S. Appl. No. 15/292,006 dated Oct. 17, 2018 (18 pages).
Notice of Allowance from the U.S. Patent and Trademark Office for U.S. Appl. No. 15/292,006 dated Nov. 29, 2018 (12 pages).
Corrected Notice of Allowability from the U.S. Patent and Trademark Office for U.S. Appl. No. 15/292,006 dated Jan. 28, 2019 (3 pages).

(56) References Cited

OTHER PUBLICATIONS

Non-Final Office Action from the U.S. Patent and Trademark Office for U.S. Appl. No. 15/292,014 dated Jan. 24, 2019 (7 pages).
Non-Final Office Action from the U.S. Patent and Trademark Office for U.S. Appl. No. 15/188,872 dated Oct. 19, 2018 (12 pages).
Notice of Allowance from the U.S. Patent and Trademark Office for U.S. Appl. No. 15/188,819 dated Jan. 25, 2019 (7 pages).
Final Office Action from the U.S. Patent and Trademark Office for U.S. Appl. No. 15/140,351 dated Dec. 6, 2018 (21 pages).
Non-Final Office Action from the U.S. Patent and Trademark Office for U.S. Appl. No. 15/140,348 dated Nov. 19, 2018 (33 pages).
Corrected Notice of Allowability from the U.S. Patent and Trademark Office for U.S. Appl. No. 15/469,281 dated Mar. 4, 2019 (8 pages).
Notice of Allowance from the U.S. Patent and Trademark Office for U.S. Appl. No. 15/292,006 dated Apr. 10, 2019 (6 pages).
Final Office Action from the U.S. Patent and Trademark Office for U.S. Appl. No. 15/475,930 dated Apr. 1, 2019 (18 pages).
Notice of Allowance from the U.S. Patent and Trademark Office for U.S. Appl. No. 15/469,281 dated Apr. 29, 2019 (10 pages).
Notice of Allowance from the U.S. Patent and Trademark Office for U.S. Appl. No. 15/469,281 dated Jan. 11, 2019 (12 pages).
Corrected Notice of Allowability from the U.S. Patent and Trademark Office for U.S. Appl. No. 15/945,448 dated Feb. 20, 2019 (2 pages).
Final Office Action from the U.S. Patent and Trademark Office for U.S. Appl. No. 15/188,872 dated May 8, 2019 (14 pages).
Notice of Allowance from the U.S. Patent and Trademark Office for U.S. Appl. No. 15/945,448 dated May 6, 2019 (7 pages).
Notice of Allowance from the U.S. Patent and Trademark Office for U.S. Appl. No. 15/346,530 dated May 15, 2019 (8 pages).
Non-Final Office Action from the U.S. Patent and Trademark Office for U.S. Appl. No. 15/140,346 dated May 28, 2019 (39 pages).
Non-Final Office Action from the U.S. Patent and Trademark Office for U.S. Appl. No. 15/140,363 dated Jun. 3, 2019 (33 pages).
Non-Final Office Action from the U.S. Patent and Trademark Office for U.S. Appl. No. 15/140,351 dated May 21, 2019 (14 pages).
Notice of Allowance from the U.S. Patent and Trademark Office for U.S. Appl. No. 15/799,657 dated May 20, 2019 (8 pages).
Interview Summary from the U.S. Patent and Trademark Office for U.S. Appl. No. 11/942,674 dated Jul. 26, 2010 (3 pages).
Applicant-Initiated Interview Summary from the U.S. Patent and Trademark Office for U.S. Appl. No. 11/942,687 dated Mar. 4, 2015 (3 pages).
Applicant-Initiated Interview Summary from the U.S. Patent and Trademark Office for U.S. Appl. No. 11/942,687 dated Jun. 17, 2014 (3 pages).
Interview Summary from the U.S. Patent and Trademark Office for U.S. Appl. No. 11/942,687 dated Jun. 10, 2011 (3 pages).
Examiner's Answer to Appeal Brief from the U.S. Patent and Trademark Office for U.S. Appl. No. 11/942,687 dated Feb. 25, 2016 (11 pages).
Patent Board Decision from the U.S. Patent and Trademark Office for U.S. Appl. No. 11/942,687 dated Dec. 22, 2017 (13 pages).
Examiner's Answer to Appeal Brief from the U.S. Patent and Trademark Office for U.S. Appl. No. 11/944,000 dated Jun. 26, 2013 (14 pages).
Patent Board Decision from the U.S. Patent and Trademark Office for U.S. Appl. No. 11/944,000 dated Mar. 23, 2016 (8 pages).
Applicant-Initiated Interview Summary from the U.S. Patent and Trademark Office for U.S. Appl. No. 13/572,552 dated Sep. 3, 2014 (3 pages).
Examiner's Answer to Appeal Brief from the U.S. Patent and Trademark Office for U.S. Appl. No. 14/043,165 dated Nov. 14, 2016 (13 pages).
Notice of Allowance from the U.S. Patent and Trademark Office for U.S. Appl. No. 15/292,006 dated Aug. 7, 2019 (6 pages).
Non-Final Office Action from the U.S. Patent and Trademark Office for U.S. Appl. No. 15/645,448 dated Jul. 29, 2019 (26 pages).
Corrected Notice of Allowability from the U.S. Patent and Trademark Office for U.S. Appl. No. 15/945,448 dated Jul. 15, 2019 (2 pages).
Non-Final Office Action from the U.S. Patent and Trademark Office for U.S. Appl. No. 15/140,348 dated Jul. 9, 2019 (21 pages).
Notice of Allowance from the U.S. Patent and Trademark Office for U.S. Appl. No. 15/346,530 dated Aug. 27, 2019 (7 pages).
Non-Final Office Action from the U.S. Patent and Trademark Office for U.S. Appl. No. 15/646,756 dated Jul. 16, 2019 (12 pages).
Notice of Allowance from the U.S. Patent and Trademark Office for U.S. Appl. No. 15/292,014 dated Jul. 11, 2019 (8 pages).
Notice of Allowance from the U.S. Patent and Trademark Office for U.S. Appl. No. 15/469,281 dated Aug. 19, 2019 (11 pages).
Notice of Allowance from the U.S. Patent and Trademark Office for U.S. Appl. No. 15/188,872 dated Aug. 23, 2019 (10 pages).
Notice of Allowability from the U.S. Patent and Trademark Office for U.S. Appl. No. 15/188,819 dated Mar. 15, 2019 (5 pages).
Notice of Allowance from the U.S. Patent and Trademark Office for U.S. Appl. No. 15/188,819 dated Aug. 21, 2019 (8 pages).
Corrected Notice of Allowability from the U.S. Patent and Trademark Office for U.S. Appl. No. 15/945,448 dated Aug. 28, 2019 (2 pages).
Notice of Allowance from the U.S. Patent and Trademark Office for U.S. Appl. No. 14/792,210 dated Jun. 17, 2019 (10 pages).
Corrected Notice of Allowability from the U.S. Patent and Trademark Office for U.S. Appl. No. 15/292,006 dated Sep. 4, 2019 (7 pages).
Non-Final Office Action from the U.S. Patent and Trademark Office for U.S. Appl. No. 15/631,291 dated Oct. 6, 2019 (12 pages).
Corrected Notice of Allowability from the U.S. Patent and Trademark Office for U.S. Appl. No. 15/346,530 dated Oct. 9, 2019 (4 pages).
Supplemental Notice of Allowability from the U.S. Patent and Trademark Office for U.S. Appl. No. 15/188,872 dated Oct. 28, 2019 (5 pages).
Supplemental Notice of Allowability from the U.S. Patent and Trademark Office for U.S. Appl. No. 15/188,819 dated Oct. 2, 2019 (4 pages).
Final Office Action from the U.S. Patent and Trademark Office for U.S. Appl. No. 15/140,346 dated Oct. 31, 2019 (41 pages).
Notice of Allowance from the U.S. Patent and Trademark Office for U.S. Appl. No. 15/292,014 dated Nov. 15, 2019 (7 pages).
Final Office Action from the U.S. Patent and Trademark Office for U.S. Appl. No. 15/140,351 dated Nov. 14, 2019 (14 pages).
Notice of Allowance from the U.S. Patent and Trademark Office for U.S. Appl. No. 14/792,210 dated Oct. 11, 2019 (9 pages).
Non-Final Office Action from the U.S. Patent and Trademark Office for U.S. Appl. No. 16/529,378 dated Oct. 22, 2019 (8 pages).
Non-Final Office Action from the U.S. Patent and Trademark Office for U.S. Appl. No. 15/140,348 dated Dec. 4, 2019 (21 pages).
Notice of Allowance from the U.S. Patent and Trademark Office for U.S. Appl. No. 15/254,627 dated Jul. 13, 2017 (4 pages).
Notice of Allowance from the U.S. Patent and Trademark Office for U.S. Appl. No. 14/540,830 dated Aug. 15, 2017 (9 pages).
Non-Final Office Action from the U.S. Patent and Trademark Office for U.S. Appl. No. 15/346,530 dated Mar. 26, 2018 (12 pages).
Examiner Interview Summary from the U.S. Patent and Trademark Office for U.S. Appl. No. 11/179,384 dated Sep. 24, 2008 (4 pages).
Examiner Interview Summary from the U.S. Patent and Trademark Office for U.S. Appl. No. 11/179,384 dated Feb. 18, 2009 (2 pages).
Examiner Interview Summary from the U.S. Patent and Trademark Office for U.S. Appl. No. 12/870,645 dated Jun. 10, 2011 (2 pages).
Non-Final Office Action from the U.S. Patent and Trademark Office for U.S. Appl. No. 11/944,000 dated Oct. 5, 2012 (11 pages).
Examiner Interview Summary from the U.S. Patent and Trademark Office for U.S. Appl. No. 11/944,000 dated Feb. 4, 2011 (3 pages).
Applicant Initiated Interview Summary from the U.S. Patent and Trademark Office for U.S. Appl. No. 14/179,328 dated Dec. 11, 2014 (3 pages).
Non-Final Office Action from the U.S. Patent and Trademark Office for U.S. Appl. No. 15/469,296 dated Jun. 27, 2017 (58 pages).
Non-Final Office Action from the U.S. Patent and Trademark Office for U.S. Appl. No. 15/469,281 dated Jun. 26, 2017 (51 pages).

(56) References Cited

OTHER PUBLICATIONS

Final Office Action from the U.S. Patent and Trademark Office for U.S. Appl. No. 15/469,281 dated Jan. 11, 2018 (60 pages).
Non-Final Office Action from the U.S. Patent and Trademark Office for U.S. Appl. No. 15/469,281 dated Apr. 2, 2018 (59 pages).
Notice of Allowance from the U.S. Patent and Trademark Office for U.S. Appl. No. 12/857,915 dated Jul. 3, 2014 (20 pages).
Notice of Allowability from the U.S. Patent and Trademark Office for U.S. Appl. No. 15/254,627 dated Jul. 13, 2017 (4 pages).
Notice of Allowance from the U.S. Patent and Trademark Office for U.S. Appl. No. 13/171,081 dated Sep. 4, 2013 (12 pages).
Notice of Allowability from the U.S. Patent and Trademark Office for U.S. Appl. No. 12/870,645 dated Dec. 7, 2011 (4 pages).
Notice of Allowance from the U.S. Patent and Trademark Office for U.S. Appl. No. 12/891,543 dated Nov. 14, 2013 (14 pages).
Notice of Allowability from the U.S. Patent and Trademark Office for U.S. Appl. No. 15/163,600 dated Sep. 14, 2016 (6 pages).
Notice of Allowability from the U.S. Patent and Trademark Office for U.S. Appl. No. 13/572,397 dated Sep. 29, 2015 (2 pages).
Notice of Allowance from the U.S. Patent and Trademark Office for U.S. Appl. No. 15/469,296 dated Jan. 22, 2018 (11 pages).
Non-Final Office Action from the U.S. Patent and Trademark Office for U.S. Appl. No. 15/475,930 dated Jan. 10, 2018 (11 pages).
Non-Final Office Action from the U.S. Patent and Trademark Office for U.S. Appl. No. 15/469,342 dated Jun. 27, 2017 (62 pages).
Notice of Allowance from the U.S. Patent and Trademark Office for U.S. Appl. No. 15/469,342 dated Nov. 30, 2017 (12 pages).
Notice of Allowance from the U.S. Patent and Trademark Office for U.S. Appl. No. 15/631,313 dated Jan. 30, 2018 (10 pages).
Office Action from the U.S. Patent and Trademark Office for U.S. Appl. No. 15/346,530 dated Mar. 26, 2018 (40 pages).
Office Action from the U.S. Patent and Trademark Office for U.S. Appl. No. 15/799,657 dated Mar. 8, 2018 (25 pages).
Notice of Allowance from the U.S. Patent and Trademark Office for U.S. Appl. No. 15/631,313 dated May 25, 2018 (10 pages).
Office Action from the U.S. Patent and Trademark Office for U.S. Appl. No. 15/945,448 dated Jul. 16, 2018 (7 pages).
Correct Notice of Allowability from the U.S. Patent and Trademark Office for U.S. Appl. No. 15/631,313 dated Jul. 20, 2018 (3 pages).
Interview Summary from the U.S. Patent and Trademark Office for U.S. Appl. No. 11/179,384 dated Sep. 24, 2008 (4 pages).
Interview Summary from the U.S. Patent and Trademark Office for U.S. Appl. No. 11/179,384 dated Feb. 18, 2009 (4 pages).
Notice of Allowance from the U.S. Patent and Trademark Office for U.S. Appl. No. 15/631,313 dated May 25, 2018 (14 pages).
Corrected Notice of Allowability from the U.S. Patent and Trademark Office for U.S. Appl. No. 15/631,313 dated Jul. 20, 2018 (7 pages).
Non-Final Office Action from the U.S. Patent and Trademark Office for U.S. Appl. No. 15/292,006 dated May 9, 2018 (17 pages).
Applicant-Initiated Interview Summary from the U.S. Patent and Trademark Office for Application No. 15/46, dated May 17, (3 pages).
Final Office Action from the U.S. Patent and Trademark Office for U.S. Appl. No. 15/346,530 dated Sep. 6, 2018 (14 pages).
Notice of Allowance from the U.S. Patent and Trademark Office for U.S. Appl. No. 14/043,165 dated Mar. 19, 2018 (11 pages).
Notice of Allowance from the U.S. Patent and Trademark Office for U.S. Appl. No. 14/043,165 dated Aug. 6, 2018 (11 pages).
Patent Board Decision from the U.S. Patent and Trademark Office for U.S. Appl. No. 14/043,165 dated Dec. 20, 2017 (11 pages).
Non-Final Office Action from the U.S. Patent and Trademark Office for U.S. Appl. No. 15/475,930 dated Jan. 10, 2018 (42 pages).
Final Office Action from the U.S. Patent and Trademark Office for U.S. Appl. No. 15/475,930 dated Jun. 1, 2018 (17 pages).
Non-Final Office Action from the U.S. Patent and Trademark Office for U.S. Appl. No. 15/475,930 dated Sep. 7, 2018 (16 pages).
Notice of Allowance from the U.S. Patent and Trademark Office for U.S. Appl. No. 15/469,342 dated Nov. 30, 2017 (11 pages).
Examiner-Initiated Interview Summary from the U.S. Patent and Trademark Office for U.S. Appl. No. 15/469,342 dated Nov. 30, 2017 (1 page).
Applicant-Initiated Interview Summary from the U.S. Patent and Trademark Office for U.S. Appl. No. 15/469,281 dated Jun. 26, 2018 (3 pages).
Final Office Action from the U.S. Patent and Trademark Office for U.S. Appl. No. 15/469,281 dated Jan. 11, 2018 (64 pages).
Final Office Action from the U.S. Patent and Trademark Office for U.S. Appl. No. 15/469,281 dated Sep. 20, 2018 (58 pages).
Non-Final Office Action from the U.S. Patent and Trademark Office for U.S. Appl. No. 15/188,819 dated Jul. 3, 2018 (7 pages).
Non-Final Office Action from the U.S. Patent and Trademark Office for U.S. Appl. No. 15/140,351 dated Jul. 30, 2018 (25 pages).
Examiner-Initiated Interview Summary from the U.S. Patent and Trademark Office for U.S. Appl. No. 12/857,915 dated Jul. 3, 2014 (1 page).
Notice of Allowance from the U.S. Patent and Trademark Office for U.S. Appl. No. 12/870,645 dated Sep. 13, 2011 (10 pages).
Interview Summary from the U.S. Patent and Trademark Office for U.S. Appl. No. 11/944,000 dated Feb. 4, 2011 (3 pages).
Examiner-Initiated Interview Summary from the U.S. Patent and Trademark Office for U.S. Appl. No. 13/768,765 dated Aug. 28, 2015 (1 page).
Examiner-Initiated Interview Summary from the U.S. Patent and Trademark Office for U.S. Appl. No. 12/891,543 dated Nov. 14, 2013 (1 page).
Applicant-Initiated Interview Summary from the U.S. Patent and Trademark Office for U.S. Appl. No. 14/179,328 dated Dec. 11, 2014 (3 page).
Examiner-Initiated Interview Summary from the U.S. Patent and Trademark Office for U.S. Appl. No. 15/163,600 dated Sep. 14, 2016 (1 page).
Corrected Notice of Allowability from the U.S. Patent and Trademark Office for U.S. Appl. No. 13/572,397 dated Jun. 29, 2015 (2 pages).
Examiner-Initiated Interview Summary from the U.S. Patent and Trademark Office for U.S. Appl. No. 15/292,006 dated Nov. 29, 2018 (1 page).
Notice of Allowance from the U.S. Patent and Trademark Office for U.S. Appl. No. 15/945,448 dated Jan. 10, 2019 (9 pages).
Examiner Interview Summary from the U.S. Patent and Trademark Office for U.S. Appl. No. 11/179,384 dated Feb. 18, 2009 (2 page).
Examiner Interview Summary from the U.S. Patent and Trademark Office for U.S. Appl. No. 11/179,384 dated Sep. 24, 2008 (4 page).
Notice of Allowance from the U.S. Patent and Trademark Office for U.S. Appl. No. 14/540,830 dated Aug. 15, 2017 (11 pages).
Final Office Action from the U.S. Patent and Trademark Office for U.S. Appl. No. 14/540,830 dated May 15, 2017 (42 pages).
Applicant-Initiated Interview Summary from the U.S. Patent and Trademark Office for U.S. Appl. No. 14/540,830 dated Jul. 28, 2017 (3 page).
Applicant-Initiated Interview Summary from the U.S. Patent and Trademark Office for U.S. Appl. No. 14/540,830 dated Mar. 24, 2017 (3 page).
Applicant-Initiated Interview Summary from the U.S. Patent and Trademark Office for U.S. Appl. No. 15/346,530 dated May 17, 2018 (3 page).
Patent Board Decision from the U.S. Patent and Trademark Office for U.S. Appl. No. 11/942,687 dated Dec. 22, 2017 (13 page).
Interview Summary from the U.S. Patent and Trademark Office for U.S. Appl. No. 11/942,687 dated Jun. 10, 2011 (3 page).
Patent Board Decision from the U.S. Patent and Trademark Office for U.S. Appl. No. 14/043,165 dated Dec. 20, 2017 (11 page).
Applicant-Initiated Interview Summary from the U.S. Patent and Trademark Office for U.S. Appl. No. 15/469,342 dated Oct. 13, 2017 (3 page).
Applicant-Initiated Interview Summary from the U.S. Patent and Trademark Office for U.S. Appl. No. 15/469,281 dated Jun. 26, 2018 (3 page).
Applicant-Initiated Interview Summary from the U.S. Patent and Trademark Office for U.S. Appl. No. 15/469,281 dated Oct. 13, 2017 (3 page).

(56) References Cited

OTHER PUBLICATIONS

Applicant-Initiated Interview Summary from the U.S. Patent and Trademark Office for U.S. Appl. No. 15/469,296 dated Oct. 13, 2017 (3 page).
Corrected Notice of Allowability from the U.S. Patent and Trademark Office for U.S. Appl. No. 15/254,627 dated Jul. 13, 2017 (4 page).
Applicant Summary of Interview of Examiner from the U.S. Patent and Trademark Office for U.S. Appl. No. 13/345,606 dated Oct. 21, 2013 (8 pages).
Notice of Allowance from the U.S. Patent and Trademark Office for U.S. Appl. No. 14/298,806 dated Apr. 12, 2017 (10 pages).
Notice of Allowance from the U.S. Patent and Trademark Office for U.S. Appl. No. 11/944,000 dated Jan. 30, 2017 (12 pages).
Interview Summary from the U.S. Patent and Trademark Office for U.S. Appl. No. 11/944,000 dated Feb. 4, 2011 (3 page).
Notice of Allowance from the U.S. Patent and Trademark Office for U.S. Appl. No. 15/292,023 dated Apr. 11, 2017 (11 pages).
Patent Board Decision from the U.S. Patent and Trademark Office for U.S. Appl. No. 12/437,522 dated Sep. 5, 2017 (12 pages).
Notice of Allowance from the U.S. Patent and Trademark Office for U.S. Appl. No. 12/437,522 dated Apr. 23, 2014 (11 pages).
Non-Final Office Action from the U.S. Patent and Trademark Office for U.S. Appl. No. 12/437,522 dated Sep. 10, 2014 (4 pages).
Non-Final Office Action from the U.S. Patent and Trademark Office for U.S. Appl. No. 12/437,522 dated Feb. 3, 2011 (16 pages).
Final Office Action from the U.S. Patent and Trademark Office for U.S. Appl. No. 12/437,522 dated Apr. 20, 2015 (5 pages).
Final Office Action from the U.S. Patent and Trademark Office for U.S. Appl. No. 12/437,522 dated Oct. 14, 2011 (17 pages).
Examiner's Answer to Appeal Brief from the U.S. Patent and Trademark Office for U.S. Appl. No. 12/437,522 dated Jul. 5, 2016 (18 pages).
Interview Summary from the U.S. Patent and Trademark Office for U.S. Appl. No. 12/437,522 dated Jun. 1, 2011 (3 page).
Applicant-Initiated Interview Summary from the U.S. Patent and Trademark Office for U.S. Appl. No. 12/437,522 dated Aug. 11, 2015 (3 page).
Notice of Allowance from the U.S. Patent and Trademark Office for U.S. Appl. No. 11/179,384 dated Nov. 3, 2009 (8 pages).
Non-Final Office Action from the U.S. Patent and Trademark Office for U.S. Appl. No. 11/179,384 dated Dec. 29, 2008 (45 pages).
Non-Final Office Action from the U.S. Patent and Trademark Office for U.S. Appl. No. 11/179,384 dated Aug. 28, 2007 (15 pages).
Final Office Action from the U.S. Patent and Trademark Office for U.S. Appl. No. 11/179,384 dated Jul. 24, 2009 (23 pages).
Final Office Action from the U.S. Patent and Trademark Office for U.S. Appl. No. 11/179,384 dated Jun. 26, 2008 (31 pages).
Interview Summary from the U.S. Patent and Trademark Office for U.S. Appl. No. 11/179,384 dated Feb. 18, 2009 (2 pages).
Notice of Allowance from the U.S. Patent and Trademark Office for U.S. Appl. No. 12/702,976 dated Jul. 20, 2011 (7 pages).
Non-Final Office Action from the U.S. Patent and Trademark Office for U.S. Appl. No. 12/702,976 dated Aug. 18, 2010 (17 pages).
Final Office Action from the U.S. Patent and Trademark Office for U.S. Appl. No. 12/702,976 dated Feb. 17, 2011 (13 pages).
Interview Summary from the U.S. Patent and Trademark Office for U.S. Appl. No. 12/702,976 dated May 31, 2011 (3 pages).
Interview Summary from the U.S. Patent and Trademark Office for U.S. Appl. No. 12/702,976 dated Dec. 1, 2010 (4 pages).
Notice of Allowability from the U.S. Patent and Trademark Office for U.S. Appl. No. 13/228,349 dated Jul. 20, 2012 (3 pages).
Notice of Allowance from the U.S. Patent and Trademark Office for U.S. Appl. No. 13/228,349 dated Feb. 6, 2012 (5 pages).
Non-Final Office Action from the U.S. Patent and Trademark Office for U.S. Appl. No. 13/228,349 dated Dec. 1, 2011 (17 pages).
Notice of Allowance from the U.S. Patent and Trademark Office for U.S. Appl. No. 13/477,853 dated Aug. 15, 2014 (7 pages).
Non-Final Office Action from the U.S. Patent and Trademark Office for U.S. Appl. No. 13/477,853 dated Dec. 11, 2013 (20 pages).
Final Office Action from the U.S. Patent and Trademark Office for U.S. Appl. No. 13/477,853 dated Jun. 13, 2014 (13 pages).
Applicant-Initiated Interview Summary from the U.S. Patent and Trademark Office for U.S. Appl. No. 13/477,853 dated Mar. 14, 2014 (3 pages).
Notice of Allowance from the U.S. Patent and Trademark Office for U.S. Appl. No. 14/540,830 dated Aug. 15, 2017 (8 pages).
Non-Final Office Action from the U.S. Patent and Trademark Office for U.S. Appl. No. 14/540,830 dated Jan. 17, 2017 (26 pages).
Applicant-Initiated Interview Summary from the U.S. Patent and Trademark Office for U.S. Appl. No. 14/540,830 dated Jul. 28, 2017 (6 pages).
Applicant-Initiated Interview Summary from the U.S. Patent and Trademark Office for U.S. Appl. No. 14/540,830 dated Mar. 24, 2017 (3 pages).
Notice of Allowance from the U.S. Patent and Trademark Office for U.S. Appl. No. 15/631,313 dated Jan. 30, 2018 (42 pages).
Corrected Notice of Allowability from the U.S. Patent and Trademark Office for U.S. Appl. No. 15/292,006 dated Jan. 28, 2019 (7 pages).
Examiner-Initiated Interview Summary from the U.S. Patent and Trademark Office for U.S. Appl. No. 15/292,006 dated Nov. 29, 2018 (35 pages).
Applicant-Initiated Interview Summary from the U.S. Patent and Trademark Office for U.S. Appl. No. 15/346,530 dated May 17, 2018 (3 pages).
Supplemental Notice of Allowability from the U.S. Patent and Trademark Office for U.S. Appl. No. 11/268,261 dated Jan. 6, 2011 (3 pages).
Notice of Allowance from the U.S. Patent and Trademark Office for U.S. Appl. No. 11/268,261 dated Dec. 3, 2010 (6 pages).
Notice of Allowance from the U.S. Patent and Trademark Office for U.S. Appl. No. 11/268,261 dated Oct. 8, 2010 (6 pages).
Supplemental Notice of Allowability from the U.S. Patent and Trademark Office for U.S. Appl. No. 11/268,261 dated Aug. 6, 2010 (4 pages).
Notice of Allowance from the U.S. Patent and Trademark Office for U.S. Appl. No. 11/268,261 dated May 17, 2010 (8 pages).
Notice of Allowance from the U.S. Patent and Trademark Office for U.S. Appl. No. 11/268,261 dated Feb. 2, 2010 (12 pages).
Non-Final Office Action from the U.S. Patent and Trademark Office for U.S. Appl. No. 11/268,261 dated Oct. 1, 2009 (35 pages).
Interview Summary from the U.S. Patent and Trademark Office for U.S. Appl. No. 11/268,261 dated Jan. 25, 2010 (3 pages).
Notice of Allowability from the U.S. Patent and Trademark Office for U.S. Appl. No. 12/857,915 dated Aug. 15, 2014 (4 pages).
Notice of Allowance from the U.S. Patent and Trademark Office for U.S. Appl. No. 12/857,915 dated Jul. 3, 2014 (19 pages).
Non-Final Office Action from the U.S. Patent and Trademark Office for U.S. Appl. No. 12/857,915 dated Aug. 23, 2013 (33 pages).
Non-Final Office Action from the U.S. Patent and Trademark Office for U.S. Appl. No. 12/857,915 dated Jun. 12, 2012 (33 pages).
Non-Final Office Action from the U.S. Patent and Trademark Office for U.S. Appl. No. 12/857,915 dated May 16, 2011 (26 pages).
Final Office Action from the U.S. Patent and Trademark Office for U.S. Appl. No. 12/857,915 dated Dec. 15, 2011 (37 pages).
Examiner-Initiated Interview Summary from the U.S. Patent and Trademark Office for U.S. Appl. No. 12/857,915 dated Jul. 3, 2014 (1 pages).
Applicant-Initiated Interview Summary from the U.S. Patent and Trademark Office for U.S. Appl. No. 12/857,915 dated Sep. 6, 2011 (3 pages).
Advisory Action from the U.S. Patent and Trademark Office for U.S. Appl. No. 11/179,384 dated Sep. 17, 2009 (3 pages).
Notice of Allowance from the U.S. Patent and Trademark Office for U.S. Appl. No. 11/265,978 dated May 3, 2010 (2 pages).
Notice of Allowance from the U.S. Patent and Trademark Office for U.S. Appl. No. 11/265,978 dated Aug. 3, 2010 (2 pages).
Interview Summary from the U.S. Patent and Trademark Office for U.S. Appl. No. 11/268,261 dated May 14, 2010 (2 pages).
Issue Notice from the U.S. Patent and Trademark Office for U.S. Appl. No. 11/268,261 dated Sep. 1, 2010 (1 page).

(56) References Cited

OTHER PUBLICATIONS

Non-Final Office Action from the U.S. Patent and Trademark Office for U.S. Appl. No. 11/942,674 dated May 26, 2010 (13 pages).
Final Office Action from the U.S. Patent and Trademark Office for U.S. Appl. No. 11/942,674 dated Nov. 26, 2010 (19 pages).
Interview Summary from the U.S. Patent and Trademark Office for U.S. Appl. No. 11/942,674 dated Mar. 2, 2011 (3 pages).
Notice of Allowance from the U.S. Patent and Trademark Office for U.S. Appl. No. 11/942,674 dated Apr. 1, 2011 (9 pages).
Non-Final Office Action from the U.S. Patent and Trademark Office for U.S. Appl. No. 11/942,687 dated Sep. 16, 2010.
Interview Summary from the U.S. Patent and Trademark Office for U.S. Appl. No. 11/942,687 dated Dec. 3, 2010.
Final Office Action from the U.S. Patent and Trademark Office for U.S. Appl. No. 11/942,687 dated Apr. 5, 2011.
Office Action from the U.S. Patent and Trademark Office for U.S. Appl. No. 11/942,687 dated Mar. 13, 2014.
Office Action from the U.S. Patent and Trademark Office for U.S. Appl. No. 11/942,687 dated Jul. 18, 2014.
Final Office Action from the U.S. Patent and Trademark Office for U.S. Appl. No. 11/942,687 dated Jan. 5, 2015.
Non-Final Office Action from the U.S. Patent and Trademark Office for U.S. Appl. No. 11/944,000 dated Sep. 29, 2010.
Final Office Action from the U.S. Patent and Trademark Office for U.S. Appl. No. 11/944,000 dated Apr. 20, 2011.
Interview Summary from the U.S. Patent and Trademark Office for U.S. Appl. No. 11/944,000 dated Jun. 7, 2011.
Advisory Action from the U.S. Patent and Trademark Office for U.S. Appl. No. 11/944,000 dated Aug. 1, 2011 (3 pages).
Appeal Brief from the U.S. Patent and Trademark Office for U.S. Appl. No. 11/944,000 dated Mar. 4, 2013.
Office Action from the U.S. Patent and Trademark Office for U.S. Appl. No. 11/944,000 dated Jul. 15, 2016.
Non-Final Office Action from the U.S. Patent and Trademark Office for U.S. Appl. No. 11/944,027 dated Apr. 14, 2010.
Interview Summary from the U.S. Patent and Trademark Office for U.S. Appl. No. 11/944,027 dated May 13, 2010.
Final Office Action from the U.S. Patent and Trademark Office for U.S. Appl. No. 11/944,027 dated Dec. 23, 2010.
Interview Summary from the U.S. Patent and Trademark Office for U.S. Appl. No. 11/944,027 dated Mar. 31, 2011.
Office Action from the U.S. Patent and Trademark Office for U.S. Appl. No. 11/944,027 dated Apr. 19, 2012.
Interview Summary from the U.S. Patent and Trademark Office for U.S. Appl. No. 11/944,027 dated Jun. 28, 2012.
Final Office Action from the U.S. Patent and Trademark Office for U.S. Appl. No. 11/944,027 dated Oct. 22, 2012.
Notice of Allowance from the U.S. Patent and Trademark Office for U.S. Appl. No. 11/944,027 dated Jun. 5, 2013.
Office Action from the U.S. Patent and Trademark Office for U.S. Appl. No. 12/622,404 dated Feb. 3, 2012.
Interview Summary from the U.S. Patent and Trademark Office for U.S. Appl. No. 12/622,404 dated May 8, 2012.
Final Office Action from the U.S. Patent and Trademark Office for U.S. Appl. No. 12/622,404 dated Aug. 6, 2012.
Notice of Allowance from the U.S. Patent and Trademark Office for U.S. Appl. No. 12/622,404 dated Oct. 15, 2012.
Office Action from the U.S. Patent and Trademark Office for U.S. Appl. No. 12/891,543 dated Mar. 4, 2013.
Interview Summary from the U.S. Patent and Trademark Office for U.S. Appl. No. 12/891,543 dated Apr. 5, 2013.
Non-Final Office Action from the U.S. Patent and Trademark Office for U.S. Appl. No. 13/079,597 dated Jan. 11, 2012 (8 pages).
Non-Final Office Action from the U.S. Patent and Trademark Office for U.S. Appl. No. 13/118,085 dated Nov. 10, 2011 (12 pages).
Interview Summary from the U.S. Patent and Trademark Office for U.S. Appl. No. 13/118,085 dated Feb. 17, 2012 (3 pages).
Final Office Action from the U.S. Patent and Trademark Office for U.S. Appl. No. 13/118,085 dated Apr. 13, 2012 (15 pages).
Notice of Allowance from the U.S. Patent and Trademark Office for U.S. Appl. No. 13/118,085 dated Feb. 6, 2013 (11 pages).
Interview Summary from the U.S. Patent and Trademark Office for U.S. Appl. No. 13/345,606 dated Aug. 15, 2013 (3 pages).
Office Action from the U.S. Patent and Trademark Office for U.S. Appl. No. 13/572,397 dated Jun. 27, 2014.
Final Office Action from the U.S. Patent and Trademark Office for U.S. Appl. No. 13/572,397 dated Jan. 13, 2015.
Notice of Allowance from the U.S. Patent and Trademark Office for U.S. Appl. No. 13/572,397 dated Mar. 19, 2015.
Office Action from the U.S. Patent and Trademark Office for U.S. Appl. No. 13/572,547 dated Aug. 6, 2014.
Notice of Allowance from the U.S. Patent and Trademark Office for U.S. Appl. No. 13/572,547 dated Mar. 3, 2015.
Notice of Allowance from the U.S. Patent and Trademark Office for U.S. Appl. No. 13/572,547 dated Apr. 10, 2015.
Notice of Allowance from the U.S. Patent and Trademark Office for U.S. Appl. No. 13/572,547 dated May 21, 2015.
Office Action from the U.S. Patent and Trademark Office for U.S. Appl. No. 13/572,552 dated Jul. 30, 2014.
Interview Summary from the U.S. Patent and Trademark Office for U.S. Appl. No. 13/572,552 dated Apr. 23, 2015.
Notice of Allowance from the U.S. Patent and Trademark Office for U.S. Appl. No. 13/572,552 dated May 8, 2015.
Office Action from the U.S. Patent and Trademark Office for U.S. Appl. No. 13/768,765 dated Mar. 17, 2015.
Interview Summary from the U.S. Patent and Trademark Office for U.S. Appl. No. 13/768,765 dated Jun. 11, 2015.
Notice of Allowance from the U.S. Patent and Trademark Office for U.S. Appl. No. 13/768,765 dated Aug. 28, 2015.
Notice of Allowance from the U.S. Patent and Trademark Office for U.S. Appl. No. 13/768,765 dated Nov. 20, 2015.
Notice of Allowance from the U.S. Patent and Trademark Office for U.S. Appl. No. 13/768,765 dated Jul. 28, 2016.
Non-Final Office Action from the U.S. Patent and Trademark Office for U.S. Appl. No. 13/907,128 dated Aug. 23, 2013 (9 pages).
Final Office Action from the U.S. Patent and Trademark Office for U.S. Appl. No. 13/907,128 dated Oct. 9, 2013 (19 pages).
Interview Summary from the U.S. Patent and Trademark Office for U.S. Appl. No. 13/907,128 dated Nov. 22, 2013 (3 pages).
Advisory Action from the U.S. Patent and Trademark Office for U.S. Appl. No. 13/907,128 dated Dec. 13, 2013 (2 pages).
Notice of Allowance from the U.S. Patent and Trademark Office for U.S. Appl. No. 13/907,128 dated Jan. 31, 2014 (10 pages).
Office Action from the U.S. Patent and Trademark Office for U.S. Appl. No. 14/043,165 dated Oct. 14, 2014.
Final Office Action from the U.S. Patent and Trademark Office for U.S. Appl. No. 14/043,165 dated Apr. 1, 2015.
Advisory Action from the U.S. Patent and Trademark Office for U.S. Appl. No. 14/043,165 dated Jul. 9, 2015 (3 pages).
Office Action from the U.S. Patent and Trademark Office for U.S. Appl. No. 14/043,165 dated Oct. 2, 2015.
Interview Summary from the U.S. Patent and Trademark Office for U.S. Appl. No. 14/043,165 dated Dec. 21, 2015.
Final Office Action from the U.S. Patent and Trademark Office for U.S. Appl. No. 14/043,165 dated Feb. 17, 2016.
Appeal Brief from the U.S. Patent and Trademark Office for U.S. Appl. No. 14/043,165 dated Jul. 15, 2016.
Restriction Requirement from the U.S. Patent and Trademark Office for U.S. Appl. No. 14/139,068 dated Jul. 28, 2015.
Office Action from the U.S. Patent and Trademark Office for U.S. Appl. No. 14/139,068 dated Mar. 11, 2016.
Notice of Allowance from the U.S. Patent and Trademark Office for U.S. Appl. No. 14/139,068 dated Sep. 21, 2016.
Office Action from the U.S. Patent and Trademark Office for U.S. Appl. No. 14/179,328 dated Sep. 11, 2014.
Notice of Allowance from the U.S. Patent and Trademark Office for U.S. Appl. No. 14/179,328 dated Jan. 14, 2015.
Office Action from the U.S. Patent and Trademark Office for U.S. Appl. No. 14/298,806 dated Dec. 29, 2014 (15 pages).
Interview Summary from the U.S. Patent and Trademark Office for U.S. Appl. No. 14/298,806 dated Mar. 2, 2015 (3 pages).

(56) References Cited

OTHER PUBLICATIONS

Final Office Action from the U.S. Patent and Trademark Office for U.S. Appl. No. 14/298,806 dated Jun. 17, 2015 (20 pages).
Office Action from the U.S. Patent and Trademark Office for U.S. Appl. No. 14/298,806 dated Feb. 16, 2016 (16 pages).
Final Office Action from the U.S. Patent and Trademark Office for U.S. Appl. No. 14/298,806 dated Jul. 21, 2016.
Office Action from the U.S. Patent and Trademark Office for U.S. Appl. No. 14/687,853 dated Aug. 13, 2015.
Notice of Allowance from the U.S. Patent and Trademark Office for U.S. Appl. No. 14/687,853 dated Feb. 25, 2016.
Notice of Allowance from the U.S. Patent and Trademark Office for U.S. Appl. No. 14/687,853 dated Jun. 2, 2016.
Non-Final Office Action from the U.S. Patent and Trademark Office for U.S. Appl. No. 14/792,210 dated Aug. 27, 2018 (53 pages).
Final Office Action from the U.S. Patent and Trademark Office for U.S. Appl. No. 14/792,210 dated Mar. 5, 2019 (17 pages).
Notice of Allowance from the U.S. Patent and Trademark Office for U.S. Appl. No. 14/792,210 dated Sep. 5, 2019 (2 pages).
Final Office Action from the U.S. Patent and Trademark Office for U.S. Appl. No. 15/140,348 dated Jun. 11, 2020 (27 pages).
Advisory Action from the U.S. Patent and Trademark Office for U.S. Appl. No. 15/140,351 dated Mar. 5, 2019 (4 pages).
Examiner-Initiated Interview Summary from the U.S. Patent and Trademark Office for U.S. Appl. No. 15/140,351 dated Mar. 5, 2019 (2 pages).
Applicant-Initiated Interview Summary from the U.S. Patent and Trademark Office for U.S. Appl. No. 15/140,351 dated Jul. 15, 2019 (3 pages).
Notice of Allowance from the U.S. Patent and Trademark Office for U.S. Appl. No. 15/140,351 dated Mar. 5, 2020 (16 pages).
Examiner-Initiated Interview Summary from the U.S. Patent and Trademark Office for U.S. Appl. No. 15/140,351 dated Mar. 5, 2020 (1 pages).
Notice of Allowance from the U.S. Patent and Trademark Office for U.S. Appl. No. 15/163,600 dated Aug. 11, 2016.
Applicant-Initiated Interview Summary from the U.S. Patent and Trademark Office for U.S. Appl. No. 15/188,819 dated Sep. 24, 2018 (4 pages).
Notice of Allowance from the U.S. Patent and Trademark Office for U.S. Appl. No. 15/188,819 dated Jan. 24, 2020 (8 pages).
Notice of Allowance from the U.S. Patent and Trademark Office for U.S. Appl. No. 15/188,819 dated Mar. 20, 2020 (4 pages).
Applicant-Initiated Interview Summary from the U.S. Patent and Trademark Office for U.S. Appl. No. 15/188,872 dated Jul. 15, 2019 (4 pages).
Notice of Allowance from the U.S. Patent and Trademark Office for U.S. Appl. No. 15/188,872 dated Jan. 23, 2020 (9 pages).
Notice of Allowance from the U.S. Patent and Trademark Office for U.S. Appl. No. 15/188,872 dated Mar. 20, 2020 (5 pages).
Notice of Allowance from the U.S. Patent and Trademark Office for U.S. Appl. No. 15/292,006 dated Aug. 22, 2019 (3 pages).
Notice of Allowance from the U.S. Patent and Trademark Office for U.S. Appl. No. 15/292,006 dated Oct. 29, 2019 (6 pages).
Notice of Allowance from the U.S. Patent and Trademark Office for U.S. Appl. No. 15/292,006 dated Dec. 12, 2019 (3 pages).
Notice of Allowance for U.S. Appl. No. 15/292,006 dated Feb. 10, 2020 (3 pages).
Notice of Allowance from the U.S. Patent and Trademark Office for U.S. Appl. No. 15/292,014 dated Dec. 5, 2019 (4 pages).
Notice of Allowance from the U.S. Patent and Trademark Office for U.S. Appl. No. 15/292,014 dated Jan. 8, 2020 (4 pages).
Notice of Allowance from the U.S. Patent and Trademark Office for U.S. Appl. No. 15/292,014 dated Jan. 23, 2020 (4 pages).
Office Action from the U.S. Patent and Trademark Office for U.S. Appl. No. 15/292,023 dated Jan. 12, 2017.
Advisory Action from the U.S. Patent and Trademark Office for U.S. Appl. No. 15/346,530 dated Nov. 21, 2018 (4 pages).
Notice of Allowance from the U.S. Patent and Trademark Office for U.S. Appl. No. 15/346,530 dated Dec. 17, 2019 (4 pages).

Summary of Interview from the U.S. Patent and Trademark Office for U.S. Appl. No. 15/469,281 dated Oct. 10, 2017 (1 pages).
Advisory Action from the U.S. Patent and Trademark Office for U.S. Appl. No. 15/469,281 dated Dec. 7, 2018 (3 pages).
Notice of Allowance from the U.S. Patent and Trademark Office for U.S. Appl. No. 15/469,281 dated Nov. 19, 2019 (11 pages).
Notice of Allowance from the U.S. Patent and Trademark Office for U.S. Appl. No. 15/469,281 dated Jan. 10, 2020 (4 pages).
Non-Final Office Action from the U.S. Patent and Trademark Office for U.S. Appl. No. 15/631,291 dated Oct. 8, 2019 (6 pages).
Notice of Allowance from the U.S. Patent and Trademark Office for U.S. Appl. No. 15/631,291 dated Jan. 10, 2020 (8 pages).
Notice of Allowance from the U.S. Patent and Trademark Office for U.S. Appl. No. 15/631,291 dated May 21, 2020 (8 pages).
Final Office Action from the U.S. Patent and Trademark Office for U.S. Appl. No. 15/646,756 dated Jan. 15, 2020 (13 pages).
Notice of Allowance from the U.S. Patent and Trademark Office for U.S. Appl. No. 15/646,756 dated May 20, 2020 (10 pages).
Final Office Action from the U.S. Patent and Trademark Office for U.S. Appl. No. 16/529,378 dated Jan. 24, 2020 (39 pages).
Notice of Allowance from the U.S. Patent and Trademark Office for U.S. Appl. No. 16/529,378 dated Apr. 7, 2020 (8 pages).
Notice of Allowance from the U.S. Patent and Trademark Office for U.S. Appl. No. 16/529,378 dated May 18, 2020 (8 pages).
AGFA HealthCare, color brochure "IMPAX 6: Digital Image and Information Management," © 2012 Agfa Healthcare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US) 2012. © 2012 Agfa HealthCare N.V. Downloaded from http://www.agfahealthcare/en/he/library/libraryopen?ID=37459801. Accessed on Feb. 9, 2015.
AMD Technologies, Inc. Catella PACS 5.0 Viewer User Manual (112 pgs), © 2010, AMD Technologies, Inc. (Doc. 340-3-503 Rev. 01), Downloaded from http://www.amdtechnologies.com/lit/cat5viewer.pdf.. Accessed on Feb. 9, 2015.
ASPYRA's Imaging Solutions, 3 page color print out. Accessed at http://www.aspyra.com/imaging-solutions. Accessed on Feb. 9, 2015.
Avreo, interWorks—RIS/PACS package, 2 page color brochure, © 2014, Avreo, Inc. (Document MR-5032 Rev. 4). Downloaded from http://www.avreo.com/Product Brochures/MR-5032Rev.%204interWORKS%20RISPACSPackage.pdf. Accessed on Feb. 9, 2015.
Bergstrom, Patrik. "Automated setup of display protocols" (2015).
BRIT Systems, BRIT PACS View Viewer, 2 page color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS) © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
Candelis, ImageGridTM: Image Management Appliance, 6 page color brochure. (AD-012 Rev. F Nov. 2012). © Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brocure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure,© 2014 CoActiv, LLC. Downloaded from http://coactiv.com/wp-content/uploads/2013/08/EXAM-PACS-BROCHURE-final-web.pdf. Accessed on Feb. 9, 2015.

(56) References Cited

OTHER PUBLICATIONS

Crowley, Rebecca et al., Development of Visual Diagnostic Expertise in Pathology: an information-processing Study, Jan. 2003, Journal of the American medical informatics Association, vol. 10, No. 1, pp. 39-51.
DR Systems DominatorTM Guide for Reading Physicians, Release 8.2. 546 pages, (TCP-000260-A), © 1997-2009, DR Systems, Inc. Downloaded from https://resources,dominator.com/assets/004/6999.pdf. Document accessed on Feb. 9, 2015.
DR Systems, DR Scheduler User Guide, Release 8.2, 410 pages (TCP-000115-A), © 1997-2009, DR Systems, Inc. Downloaded from https://resources.dominator,com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007:1 19-24.
FUJIFILM Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation/pdf. Accessed on Feb. 9, 2015.
FUJIFILM Medical Systems, SYNAPSE® Product Data, Synapse Release Version 3.2.1, Server Modules and Interfaces, 4 page color brochure, (XBUSSY085) Aug. 2008. Downloaded from http:www.fujifilmusa.com/shared/bin/server-interface.pdf. Accessed on Feb. 9, 2015.
FUJIFILM Medical Systems, SYNAPSE® Product Data, Synapse Release Version 3.2.1, Workstation Software, 4 page color brochure (XBUSSY082) Aug. 2008. Downloaded rom http://www.fujifilmusa.com/share/bin/workstation.pdf. Accessed on Feb. 9, 2015.
GE Healthcare, Centricity PACS, in 8 page printout. Accessed at http://www.gehealthcare.com/en/products/categories/healthcare_it/medical_imagining-informatics_-_ris-pacs-cvis/centricity_pacs. Accessed on Feb. 9, 2015.
Handlylife.com—Features of Handy Patients Enterprise, in 4 page printout. Accessed from http://www.handylife.com/en/software/features.html. Accessed on Feb. 18, 2015.
Handylife.com—Overview of Handy Patients Enterprise, in 2 page printout. Accessed from http://www.handylife.com/en/software/overview.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
ICRco, I See The Future, in 12 pages, color brochure, (BR080809AUS) © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#I■products-services/ctnu. Accessed on Feb. 9, 2015.
Infinitt, PACS, RIS Mammo PACS, Cariology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incorporated. Downloaded http://www.intelerad.com/wp-content/uploads/sites/2/2014/08/IntelPACS-brocure.pdf. Accessed on Feb. 9, 2015.
Intelerad, InteleViewer, 2 page color brochure, © 2014 Intelerad Medical Systems Incorporated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded form http://www.intuitiveimaging.com/2013/pdf/ImageQube%20one-sheet.pdf. Accessed on Feb. 9, 2015.
Ivetic, D . . . , and Dragan, D., Medical Image on the Go!, 2009, J Med Syst, vol. 35, pp. 499-516.
Kuhl, Helen: Comparison Chart/PACS, Customers Are Happy, But Looking for More, (color) Imaging Technology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS, 5.0 Web Viewer, Cariopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.
LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/poviders/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure © 2006-2014 Medweb. Downloaded from http://www.medweb.com/docs/rispacs_brochure_2014.pdf. Accessed on Feb. 9, 2015.
Mendelson, et al., "informatics in Radiology—Image Exchange: IHE and the Evolution of Image Sharing," RadioGraphics, Nov.-Dec. 2008, Vo. 28, No. 7.
Merge Radiology Solutions, Merge PACS, A real-time picture archiving communication system, (PAX-21990 rev 2.0) 2 page color brochure. Downloaded from http:/www.merge.com/MergeHealthcare/media/documents/brocures/Merge_PACS_web.pdf. Accessed on Feb. 9, 2015.
NOVARAD Enterprise Imaging Solutions, NOVAPACS, 2 page (color) printout. Accessed at http://www.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/producst_01.html. Accessed on Feb. 9, 2015.
Philips IntelliSpace PACS, in 2 color page printout. Accessed at http://www.healthcare.philips.com/main/products/healthcare_informatics/products/enterprise_imaging_informatics/isite_pacs. Accessed on Feb. 9, 2015.
Philips, IntelliSpace; Multi-modality tumor tracking application versus manual PACS methods, A time study for Response Evaluation Criteria in Solid Tumors (RECIST). 2012, Koninkliijke Philips Electronics N.V., in four pages.
Radcliffe, et al., "Comparison of Stereo Disc Photographs and Alternation Flicker Using a Novel Matching Technology for Detecting Glaucoma Progression", Ophthalmic Surgery, Lasers & Imaging, Jun. 9, 2010.
RamSoft, RIS PACS Teleradiology, PowerServer PACS, Lite PACS, XU PACS Compare RamSoft PACS Products, 2 color page printout. Accessed at http://www.ramsoft.com/products/powerserver-pacs-overview. Accessed on Feb. 9, 2015.
Rosset et al.: OsiriX: An Open-Source Software for Navigating in Multidimensional DICOM Images, Journal of digital Imaging, Sep. 2004, pp. 205-216.
Sage Intergy PACS | Product Summary. Enhancing Your Workflow by Delivering Web-based Diagnostic Images When and Where You Need them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Sandberg et al., "Automatic detection and notification of "wrong patient—wrong location" errors in the operatin room," Surgical Innovation, Sep. 2005, vol. 12, No. 3, pp. 253-260.
Schellingerhout, Dawid, MD, et al.: "Coregistration of Head CT Comparison Studies: Assessment of Clinical Utility," Acad Radiol 2003; 10:242-248.

(56) References Cited

OTHER PUBLICATIONS

Scimage, Cardiology PACS, in 8 color page printout. Accessed at http://www.scimage.com/solutions/clinical-solutions/cardiology. Accessed on Feb. 9, 2015.
Sectra RIS PACS, in 2 color page printout. Accessed at http://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaginig-it/imagining-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Sprawls, "Image Characteristics and Quality," Physical Principles of Medical Imaging, http://www.sprawls.org/resources pp. 1-14.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, Office PACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
Syed, et al., "Automated alternation flicker for the detection of optic disc haemorrhages", ACTA Ophthalmologica 2012, accepted for publication on Nov. 26, 2010.
Syed, et al., "Detection of Progressive Glaucomatous Optic Neuropathy Using Automated Alternation Flicker With Stereophotography," Research Letter, Arch Ophthalmol., published online Dec. 13, 2010. 2010 American Medical Association.
Tahmoush, D. and Samet, H., A New Database for Medical Images and Information, 2007, Medical Imaging 2007; PACS and Imaging Informatics, vol. 6516, pp. 1-9.
Tay, et al., "Assessing Signal Intensity Change on Well-registered Images: Comparing Subtraction, Color-encoded Subtraction, and Parallel Display Formats", Original Research: Computer Applications Radiology, vol. 260: No. 2—Aug. 2011.
TeraRecon iNtuition—Workflow <www.terarecon.com/wordpress/our-solutions/intuition-workflow> Last accessed Nov. 8, 2013, 2 pages.
TeraRecon iNtuition pamphlet in 20 pages, retrieved on Nov. 8, 2013, available at http://int.terarecon.com/wp-content/uploads/2013/11/brochure_english2013.pdf.
UltraRAD—ultra VISION, 1 page (color) Downloaded from http://www.ultraradcorp.com/pdf/UltraVISION.pdf. Accessed on Feb. 9, 2015.
VanderBeek, et al., "Comparing the detection and agreement of parapapillary atrophy progression using digital optic disk photographs and alternation flicker", Glaucoma, Graefes Arch Clin Exp Ophthalmol (2010) 248:1313-1317, Apr. 15, 2010.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vistek Opal-RAD, 4 color page printout. Accessed at http://vistek.net/products/opal-rad. Accessed on Feb. 9, 2015.
Voyager Imaging—Voyager PACS Radiologist Workstation, 2 page color brochure. Downloaded from http://www.intellirad.com/au/assets/Uploads/Voyager-PacsWorkstations.pdf? Accessed on Feb. 9, 2015.
Voyager Imaging—Voyager PACS, 3 page color brochure. Downloaded from http://www.intellirad.com/au/index.php/assets/Uploads/Voyager-Pacs3.pdf. Accessed on Feb. 9, 2015.
Notice of Allowance from the U.S. Patent and Trademark Office for U.S. Appl. No. 15/646,756 dated Sep. 2, 2020 (5 pages).
Notice of Allowance from the U.S. Patent and Trademark Office for U.S. Appl. No. 15/140,348 dated Sep. 3, 2020 (8 pages).
Notice of Allowance from the U.S. Patent and Trademark Office for U.S. Appl. No. 15/140,348 dated Oct. 15, 2020 (8 pages).
Notice of Allowance from the U.S. Patent and Trademark Office for U.S. Appl. No. 15/140,351 dated Sep. 22, 2020 (8 pages).
Notice of Allowance from the U.S. Patent and Trademark Office for U.S. Appl. No. 15/140,351 dated Oct. 19, 2020 (2 pages).
Final Office Action from the U.S. Patent and Trademark Office for U.S. Appl. No. 15/140,363 dated Mar. 23, 2021 (27 pages).
Notice of Allowance from the U.S. Patent and Trademark Office for U.S. Appl. No. 16/817,963 dated Apr. 15, 2021 (8 pages).
Notice of Allowance from the U.S. Patent and Trademark Office for U.S. Appl. No. 16/817,963 dated May 17, 2021 (5 pages).

* cited by examiner

SYSTEMS AND METHODS FOR MATCHING, NAMING, AND DISPLAYING MEDICAL IMAGES

CROSS-REFERENCE TO RELATED APPLICATIONS

This application is a continuation of U.S. patent application Ser. No. 15/346,530, filed Nov. 8, 2016, and entitled "SYSTEMS AND METHODS FOR MATCHING, NAMING, AND DISPLAYING MEDICAL IMAGES," which is a continuation of U.S. application Ser. No. 14/244,431, filed Apr. 3, 2014, entitled "SYSTEMS AND METHODS FOR MATCHING, NAMING, AND DISPLAYING MEDICAL IMAGES," now U.S. Pat. No. 9,542,082, which is a continuation of U.S. application Ser. No. 13/345,606, filed Jan. 6, 2012, entitled "SYSTEMS AND METHODS FOR MATCHING, NAMING, AND DISPLAYING MEDICAL IMAGES," now U.S. Pat. No. 8,731,259, which is a continuation of U.S. application Ser. No. 12/870,645, filed Aug. 27, 2010, entitled "SYSTEMS AND METHODS FOR MATCHING, NAMING, AND DISPLAYING MEDICAL IMAGES," now U.S. Pat. No. 8,094,901, which is a continuation of U.S. application Ser. No. 11/265,978, filed Nov. 3, 2005, entitled "SYSTEMS AND METHODS FOR MATCHING, NAMING, AND DISPLAYING MEDICAL IMAGES," now U.S. Pat. No. 7,787,672, which claims priority under 35 U.S.C. § 119(e) to U.S. Provisional Application Ser. No. 60/625,690, filed on Nov. 4, 2004, each of which are hereby expressly incorporated by reference in their entireties and for all purposes.

BACKGROUND OF THE INVENTION

Field of the Invention

This invention relates to matching, naming, and displaying medical images based upon user-defined rules.

Description of the Related Art

Medical imaging is increasingly moving into the digital realm. This includes imaging techniques that were traditionally analog, such as mammography, x-ray imaging, angiography, endoscopy, and pathology, where information can now be acquired directly using digital sensors, or by digitizing information that was acquired in analog form. In addition, many imaging modalities are inherently digital, such as MRI, CT, nuclear medicine, and ultrasound. Increasingly these digital images are viewed, manipulated, and interpreted using computers and related computer equipment. When medical images are created, they are typically provided an identifier, label, or name. This name can be either automatically generated or provided by a technician. One problem with organizing medical images from different sources is that these identifiers do not necessarily provide a good description that is understandable to a subsequent viewer of the image. Furthermore, as the number of images increase, there is a need for improved methods of matching related medical images together for subsequent viewing and analysis.

SUMMARY OF THE INVENTION

One embodiment comprises a method of displaying medical data. The method comprises receiving a plurality of medical images of a first medical examination and receiving at least one user-defined matching rules, at least one of user-defined matching rules identifying selection criteria for the medical images. The method also comprises selecting medical images that satisfy the selection criteria of the user-defined rules, thereby matching medical images according to user-specific rules and receiving at least one user-defined display rule, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Another embodiment comprises a method displaying medical data. The method comprises receiving a plurality of medical images of a first medical examination and receiving a plurality of medical images of a second medical examination. The method also comprises receiving at least one user-defined matching rule, at least one of user-defined matching rules identifying selection criteria for matching the medical images of the first and second medical examinations. The method also comprises selecting medical images that satisfy the selection criteria of the user-defined rules, thereby matching medical images of the first medical examination with medical images of the second examination according to user-specific rules. The method also comprises receiving a plurality of user-defined display rules, at least one of user-defined display rules identifying a display preference with respect to selected medical images. The method also comprises displaying the selected medical images according to the identified display preferences, thereby allowing matched medical images to be visually compared and displayed in a manner that is suitable to the user's preferences.

Another embodiment comprises a system for displaying medical data. The system comprises an electronic device being configured to receive a plurality of medical images of a first medical examination. The electronic device is configured to receive a plurality of user-defined matching rules. At least one of user-defined matching rules identify selection criteria for the medical images. The electronic device is further configured to select medical images that satisfy the selection criteria of the user-defined rules, thereby matching medical images according to user-specific rules. The electronic device is further configured to receive at least one user-defined display rules. At least one of user-defined display rules identify a display preference with respect to selected medical images. The electronic device is further being configured to display the selected medical images according to the identified display preferences, thereby allowing matched medical images to be visually compared and displayed in a manner that is suitable to the user's preferences.

DETAILED DESCRIPTION OF EMBODIMENTS OF THE INVENTION

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
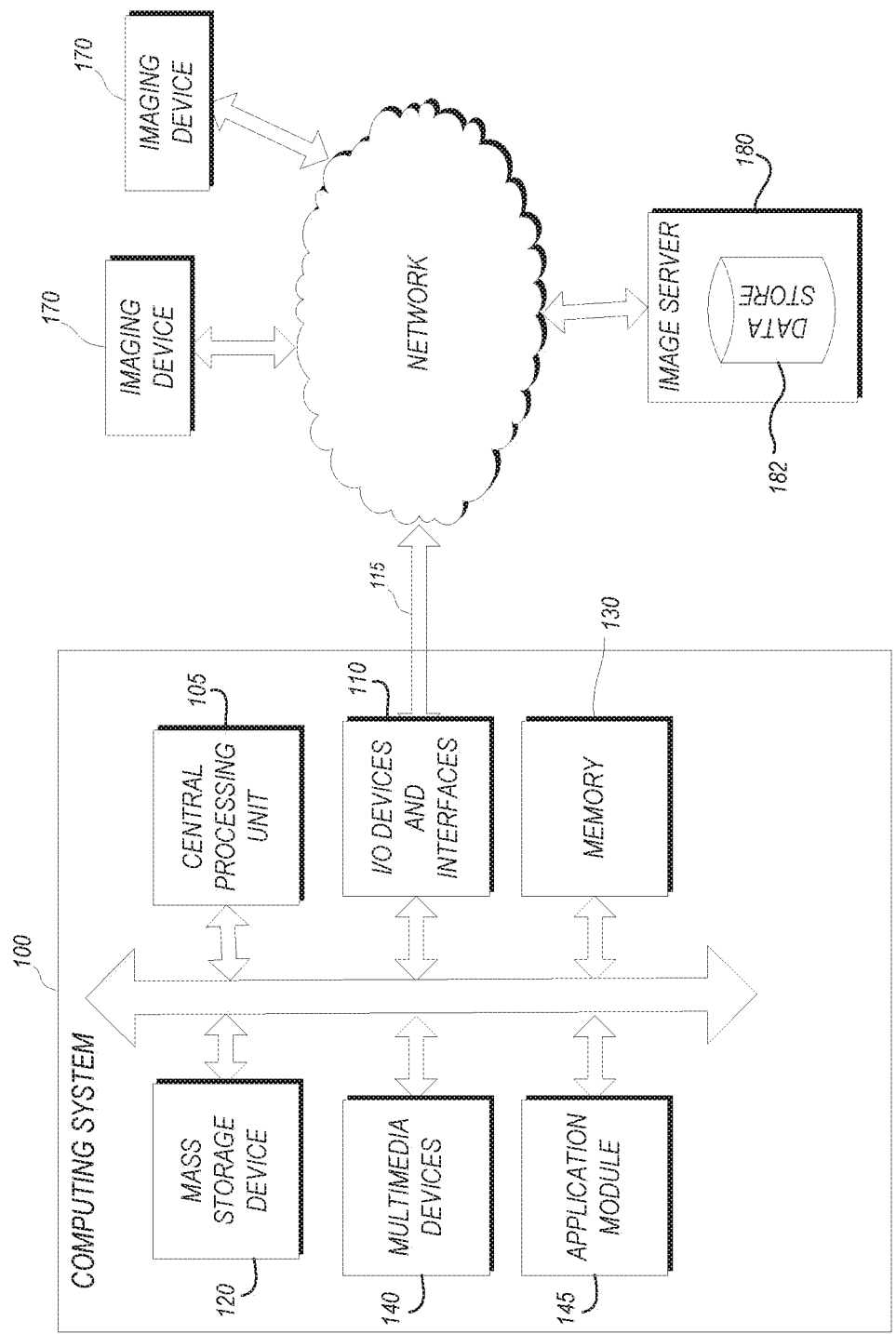
FIG. 1 is a block diagram of an exemplary computing system in communication with a network and various networked devices.

FIG. 1 is a block diagram of an exemplary computing system 100 in communication with a network 160 and various network devices. The computing system 100 may be used to implement certain systems and methods described herein. The functionality provided for in the components and modules of computing system 100 may be combined into fewer components and modules or further separated into additional components and modules.

The computing system 100 includes, for example, a personal computer that is IBM, Macintosh, or Linux/Unix compatible. In one embodiment, the exemplary computing system 100 includes a central processing unit ("CPU") 105, which may include a conventional microprocessor, an application module 145 that comprises one or more various applications that may be executed by the CPU 105. The application module 145 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

The computing system 100 further includes a memory 130, such as random access memory ("RAM") for temporary storage of information and a read only memory ("ROM") for permanent storage of information, and a mass storage device 120, such as a hard drive, diskette, or optical media storage device. Typically, the modules of the computing system 100 are connected to the computer using a standards-based bus system. In different embodiments of the present invention, the standards based bus system could be Peripheral Component Interconnect (PCI), Microchannel, SCSI, Industrial Standard Architecture (ISA) and Extended ISA (EISA) architectures, for example.

The computing system 100 is generally controlled and coordinated by operating system software, such as the Windows 95, 98, NT, 2000, XP or other compatible operating systems. In Macintosh systems, the operating system may be any available operating system, such as MAC OS X. In other embodiments, the computing system 100 may be controlled by a proprietary operating system. Conventional operating systems control and schedule computer processes for execution, perform memory management, provide file system, networking, and I/O services, and provide a user interface, such as a graphical user interface ("GUI"), among other things.

The exemplary computing system 100 includes one or more of commonly available input/output (I/O) devices and interfaces 110, such as a keyboard, mouse, touchpad, and printer. In one embodiment, the I/O devices and interfaces 110 include one or more display devices, such as a monitor, that allows the visual presentation of data to a user. More particularly, display devices provide for the presentation of GUIs, application software data, and multimedia presentations, for example. In one embodiment, a GUI includes one or more display panes in which medical images may be displayed. According to the systems and methods described below, medical images may be stored on the computing system 100 or another device that is local or remote, displayed on a display device, and manipulated by the application module 145. The computing system 100 may also include one or more multimedia devices 140, such as speakers, video cards, graphics accelerators, and microphones, for example.

In the embodiment of FIG. 1, the I/O devices and interfaces 110 provide a communication interface to various external devices. In the embodiment of FIG. 1, the computing system 100 is coupled to a network 160, such as a LAN, WAN, or the Internet, for example, via a communication link 115. The network 160 may be coupled to various computing devices and/or other electronic devices. In the exemplary embodiment of FIG. 1, the network 160 is coupled to imaging devices 170, an image server 180, and a medical facility 190. In addition to the devices that are illustrated in FIG. 1, the network 160 may communicate with other computing, imaging, and storage devices.

The imaging devices 170 may be any type of device that is capable of acquiring medical images, such as an MRI, x-ray, mammography, or CT scan systems. The image server 180 includes a data store 182 that is configured to store images and data associated with images. In one embodiment, the imaging devices 170 communicate with the image server 180 via the network 160 and image information is transmitted to the image server 180 and stored in the data store 182. In one embodiment, the image data is stored in Digital Imaging and Communications in Medicine ("DICOM") format. The complete DICOM specifications may be found on the National Electrical Manufactures Association Website at <medical.nema.org>. Also, *NEMA PS 3—Digital Imaging and Communications in Medicine,* 2004 ed., Global Engineering Documents, Englewood Colo., 2004, provides an overview of the DICOM standard. Each of the above-cited references is hereby incorporated by reference in their entireties. In one embodiment, the data store 182 also stores the user-defined display rules associated with one or more of the images stored on the data store 182. As discussed in further detail below, the user-defined display rules may vary depending of the type of image, area imaged, clinical indication, source of image, display device, user, or other factors. Accordingly, any type of user-defined display rule is expressly contemplated for use in conjunction with the systems and methods described herein.

The exemplary image server 160 is configured to store images from multiple sources and in multiple formats. For example, the image server 160 may be configured to receive medical images in the DICOM format from multiple sources, store these images in the data store 182, and selectively transmit medical images to requesting computing devices.

The medical facility 190 may be a hospital, clinic, doctor's office, or any other medical facility. The medical facility 190 may include one or more imaging devices and may share medical images with the image server 180 or other authorized computing devices. In one embodiment, multiple computing systems, such as the computing system 100 may be housed at a medical facility, such as medical facility 190.

Definition of Terms

Below is a definition of certain terms used herein.

"Modality" is defined as a medical imaging device (a patient who undergoes an MRI is said to have been examined or scanned with the MRI modality).

"Medical image" is defined to include an image of an organism. It may include but is not limited to a radiograph, computed tomography (CT), magnetic resonance imaging (MRI), Ultrasound (US), mammogram, positron emission tomography scan (PET), nuclear scan (NM), pathology, endoscopy, ophthalmology, or many other types of medical images. While this description is directed to viewing and tracking of medical images, the methods and systems described herein may also be used in conjunction with non-medical images, such as, images of circuit boards, airplane wings, and satellite images, for example.

"Patient" refers to an individual who undergoes a medical imaging examination.

"Viewing" is defined to include the process of visually observing one or more medical images associated with exams.

"Viewer" is defined as any person who views a medical image.

"Reading" is defined to include the process of visually observing one or more medical images for the purpose of creating a professional medical report, also called an interpretation. When reading is complete, an exam may be labeled "read," indicating that the medical professional has completed observation of the one or more medical images for purposes of creating a medical report.

"Reader" is defined to include one who is authorized to perform the reading process.

"User" is defined to include any person that is a viewer and/or a reader.

"Display rules" are defined to include methods of display of an image or exam. For example, an image or exam may be displayed with a certain pixel window level or width (similar to brightness and contrast), in color, based on a certain color map, opacity map, or other display parameters.

"User-defined display rules" refers to rules that a user can establish and store in a database that establish criteria for image display that is considered adequate. For example, a user-defined display rule might store a rule that triggers certain warnings or displays if all pixels in a medical image have not been displayed or, alternatively, if at least a predetermined portion of the pixels have not been displayed with a certain display method (such as image window, level, brightness, contrast, opacity, color look-up table, or other parameters). User-defined display rules may also refer to other image processing functions, such as edge enhancement and automated image analysis functions, e.g., computer-aided detection (CAD) techniques.

Figure 2:
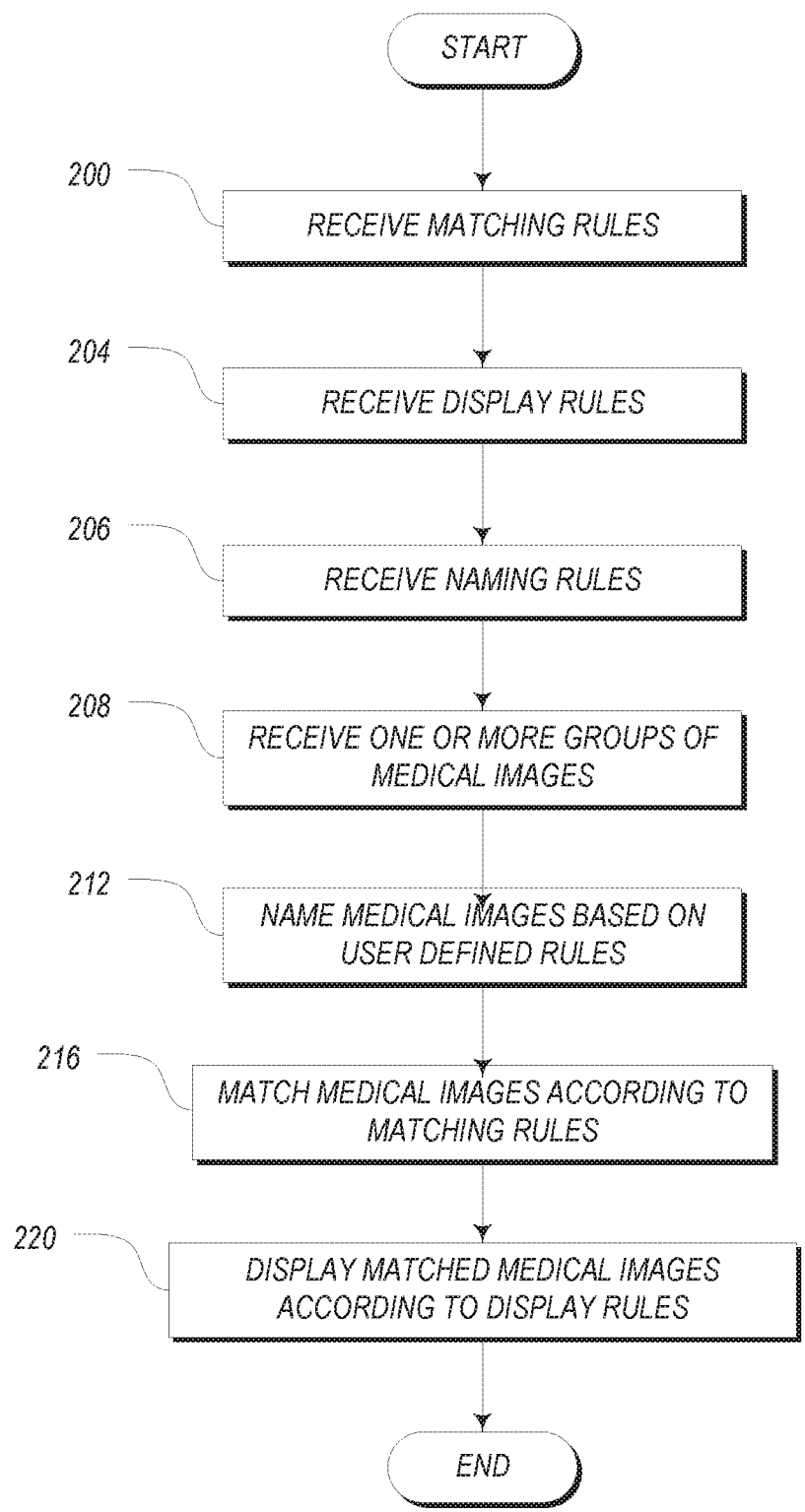
FIG. 2 is a flowchart illustrating an exemplary process of matching and displaying medical images.

FIG. 2 is a high-level flowchart describing an exemplary method that may be performed by the computing system 100 (FIG. 1). Depending on the embodiment, additional steps may be added, others removed, and the ordering of the steps rearranged.

Starting at step 200, matching rules are provided with respect to medical images that are accessible by the computer system 100. The medical can be accessible via the imaging server 180, be local to the computing system 100, or elsewhere accessible via the network 160. The matching rules establish criteria for matching related medical images. In one embodiment, the matching rules are defined for a particular individual or machine. In another embodiment, the matching rules are defined for a group or class of individuals. The rules may be provided by the users themselves and/or by a system administrator. The auto-matching rules may be established to select medical data based upon any of the following non-limiting criteria: modality (MRI, CT, X-ray etc); exam type (left knee X-ray, CT Chest, MRI Brain etc); archive status (has the exam been archived, archived and restored, not yet archived); assigned physician (has the exam been assigned to a particular physician for interpretation); exam age (how long ago was the exam done); patient age; and any item in a DICOM header file, such as orientation, contrast use, thickness of slices, field of view, MRI tissue contrast weighting, and other items. With regard to some criteria, such as MRI tissue contrast weighting, the rules may analyze the MRI pulse sequence and the imaging parameters in order to determine the tissue contrast weighting and subcategorize images into weighting categories or weighting names.

The matching rules can be used to match medical images in the same and/or different medical series. For example, assume the medical images relate to three series of 6 x-rays. The matching rules can be established such that like views amongst each of the different series are grouped together for subsequent viewing. The matching rules be defined using simple or complex search expressions such "AND" or "OR." Complex filter criteria may be stored on the image server 180 and then used by local devices that access these records via the web.

Next, at a step 204, display rules are provided with respect to the medical images. In one embodiment, the display rules may be user-defined allowing the user to determine the timing, positioning, and size of displayed matched images. For example, a user can define that matched medical images are all displayed concurrently on a display. Also, for example, a user can define that the most recent of the matched medical images are displayed on the left hand portion of the display and the other matched medical images are displayed in sequence on the right hand side of the display, the sequence advancing in response to user prompting. In one embodiment, the display rules include directives (timing, positioning, and size). As an example, directives can include the following for identifying location information: TOP_DISPLAY, BOTTOM_DISPLAY, RIGHT_DISPLAY, LEFT_DISPLAY, CENTER_DISPLAY. Furthermore, if the number of matched medical images is variable, the display rules can include instructions for identifying selected medical images based upon further rules, such as using the matching criteria listed above. In addition, the display rules may or may not define how many images or image series are displayed per monitor, a display grid (2×3, 5×4, etc.), or whether like images are displayed neighboring each other side by side horizontally or vertically. Furthermore, the display rules may also specify how different matched medical images from different series may be "interleaved" together for successive display. Using the computing system 100, a user may also manually interleave matched medical images, e.g., order the matched medical images for progressive display of each of the matched sets. The computing system 100 may also provide an interface to re-order images or image series to facilitate the matching display, and may even reorient images (flip, rotate) in order to best match the display. Using the display rules, the user can provide display rules such that related medical images are readily comparable.

In one embodiment, display rules may be set to display pre and post contrast axial T1 weighted images from a brain MRI from the same exam in adjacent panes on a monitor. Display rules may also be set to display axial T2 weighted MRI images from a prior spine MRI adjacent to axial T2 weighted images from the current exam. Display rules may also be set to display a PA projection from a chest radiograph from a prior exam adjacent to the same projection from the current exam.

Continuing to a step 206, naming rules are provided. The naming rules describe how the medical images can be provided a new "name", label, or identifying description. In one embodiment, the naming rules are defined for a particular individual or machine. In another embodiment, the matching rules are defined for a group or class of individuals. The rules may be provided by the users themselves and/or by a system administrator. The naming rules can define sets of naming rules for different exam types or other classifications. The naming rules can also be defined to perform naming before or after the matching step 216. In one embodiment, the naming rules define how information in a header file, e.g., DICOM file, that is associated with the medical image is described. The naming rules can define that the new name of the medical image is defined using meta or other data that is associated with the medical images. It is noted that the new name of the medical image need not be stored with the image but such information can be stored by any device connected to the network.

Continuing to a step 208, in one embodiment, the medical images are received by the computing system 100. It is noted that in one embodiment, the medical images need not be stored locally by the computer system 100 but are merely made accessible to it via the network. Continuing to a step 212, the computing system 100 may optionally name the received medical images based upon the received user-specific naming rules. In one embodiment, the new "names" of the medical images may be used by the computing system 100 to facilitate matching (step 216) of related medical images. In one embodiment, the naming rules define how information in a header file, e.g., a DICOM file, is described. The naming rules can define that the "new" name of the medical image is defined using meta or other data that is associated with the medical image. For example, the naming rules can define that the new "name" of the medical image is based upon the name of patient, the exam type, and the date of the medical image. Also for example, the naming rules can define categorization tables that define a particular name when certain conditions are met. The particular name can be predefined and/or based upon meta or other data that is associated with the medical images.

Proceeding to a step 216, the computing system 100 matches medical images in the same or related series together as discussed above (step 200). The matched images may be collectively or individually provided a new name per the naming rules provided in step 206. Continuing to a step 220, the matched medical images are displayed. It is noted that the display rules may define user display preferences that are specific for particular types of medical images, e.g., the imaging modality, the body part, whether there is one exam, two, or more medical images being displayed. The display rules may be defined per individual user, site, or system. In one embodiment, the user can store the display rules in a database. In one embodiment, one set of display rules can apply to one modality and another set of display rules can apply to another modality. In addition, the display rules may include specific triggers or warnings that occur if the user-defined display rules are not satisfied.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A computing system comprising:
one or more hardware computer processors;
one or more software modules configured for execution by the one or more hardware computer processors to cause the computing system to:
receive a first imaging series including images of a first modality from a first imaging center;
receive a second imaging series including images of the first modality from a second imaging center;
receive at least one user-defined naming rule for images of the first modality based on DICOM attributes of each of the images of the first modality; and
replace existing names of respective images of the first and second imaging series, or append to existing names of the images of the first and second image series, with updated names according to the at least one user-defined naming rule, wherein the updated names are based on one or more DICOM attributes of respective images.

2. The computing system of claim 1, wherein the one or more software modules are further configured for execution by the one or more hardware computer processors to cause the computing system to find matching related images using the updated names.

3. The computing system of claim 2, wherein the one or more software modules are configured to find the matching related images using the updated names via one or more matching rules.

4. The computing system of claim 3, wherein the one or more matching rules are defined for at least one selected from a group consisting of a particular user, a particular machine, or a group or class of users.

5. The computing system of claim 3, wherein the one or more matching rules find the matching related images by matching images based on at least one selected from a group consisting of modality, exam type, archive status, assigned physician, exam age, patient page, and an item in a DICOM header file.

6. The computing system of claim 5, wherein the item in the DICOM header file includes at least one selected from a group consisting of orientation, contrast use, thickness of slices, field of view, and tissue contrast weighting.

7. The computing system of claim 6, wherein the one or more software modules are configured for execution by the one or more hardware computer processors to cause the computing system to analyze a pulse sequence and at least one imaging parameter of an image to determine the tissue contrast weighting and subcategorize the image into weighting categories or weighting names.

8. The computing system of claim 3, wherein the one or more matching rules match images in the same or different medical series.

9. The computing system of claim 3, wherein the one or more matching rules match images such that like views amongst each of a plurality of different series are grouped together for subsequent viewing.

10. The computing system of claim 3, wherein the one or more matching rules are defined using one or more search expressions.

11. The computing system of claim 3, wherein the one or more software modules are further configured for execution by the one or more hardware computer processors to cause the computing system to name the matching related images collecting or individually using the at least one user-defined naming rule.

12. The computing system of claim 2, wherein the one or more software modules are further configured for execution by the one or more hardware computer processors to cause the computing system to display the matching related images based on one or more display rules.

13. The computing system of claim 12, wherein the one or more display rules are user-defined.

14. The computing system of claim 12, wherein the one or more display rules define at least one selected from a group consisting of timing, positioning, and size of the matching related images.

15. The computing system of claim 12, wherein the one or more display rules include rules for selecting a subset of the matching related images to display.

16. The computing system of claim 12, wherein the one or more display rules includes rules for interleaving images from different image series.

17. The computing system of claim 12, wherein the one or more display rules include one or more triggers for warnings when a display rule is not satisfied.

18. The computing system of claim 1, wherein the one or more DICOM attributes include at least one selected from a group consisting of patient name, an exam type, and a date of an image.

19. The computing system of claim 1, wherein the common naming format includes a categorization table that defines a particular name when one or more certain conditions are met.

20. The computing system of claim 19, wherein the particular name is predetermined or based on data associated with an image.

* * * * *